(12) United States Patent
Ahmadi Noorbakhsh

(10) Patent No.: US 11,712,531 B2
(45) Date of Patent: Aug. 1, 2023

(54) RESUSCITATION MANAGEMENT SYSTEM FOR MANUAL RESUSCITATORS

(71) Applicant: Siavash Ahmadi Noorbakhsh, Tehran (IR)

(72) Inventor: Siavash Ahmadi Noorbakhsh, Tehran (IR)

( * ) Notice: Subject to any disclaimer, the term of this patent is extended or adjusted under 35 U.S.C. 154(b) by 295 days.

(21) Appl. No.: 17/210,848

(22) Filed: Mar. 24, 2021

(65) Prior Publication Data

US 2021/0205556 A1 Jul. 8, 2021

Related U.S. Application Data

(60) Provisional application No. 62/993,728, filed on Mar. 24, 2020.

(51) Int. Cl.
*A61M 16/00* (2006.01)
*G06K 7/10* (2006.01)
*G06K 19/077* (2006.01)

(52) U.S. Cl.
CPC .... *A61M 16/0084* (2014.02); *A61M 16/0078* (2013.01); *G06K 7/10366* (2013.01); *G06K 19/07758* (2013.01); *A61M 2205/0272* (2013.01); *A61M 2205/3317* (2013.01); *A61M 2205/3327* (2013.01); *A61M 2205/3334* (2013.01); *A61M 2205/502* (2013.01); *A61M 2205/52* (2013.01); *A61M 2205/581* (2013.01); *A61M 2205/582* (2013.01); *A61M 2205/583* (2013.01); *A61M 2205/6054* (2013.01); *A61M 2230/40* (2013.01)

(58) Field of Classification Search
CPC .......... A61M 16/0084; A61M 16/0078; A61H 31/004; A61B 5/087
See application file for complete search history.

(56) References Cited

U.S. PATENT DOCUMENTS

2017/0197047 A1* 7/2017 Minato ............. A61M 16/0078

* cited by examiner

*Primary Examiner* — Courtney B Fredrickson
(74) *Attorney, Agent, or Firm* — Bajwa IP Law Firm; Haris Zaheer Bajwa

(57) ABSTRACT

A resuscitation management system may include a first accelerometer and a second accelerometer mounted on opposite sides of a resuscitation bag of a manual resuscitation device. The resuscitation management system may include a processing unit that may be configured to receive the measured acceleration vectors from the first accelerometer and the second accelerometer and then subtract the measured acceleration vectors from each other to obtain a resultant acceleration vector representing an acceleration magnitude and a spatial acceleration direction of compression/decompression of the resuscitation bag. The processing unit may then be configured to calculate the breathing parameters based at least in part on the acceleration magnitude and the spatial acceleration direction of compression/decompression of the resuscitation bag.

13 Claims, 14 Drawing Sheets

RESUSCITATION MANAGEMENT SYSTEM FOR MANUAL RESUSCITATORS

CROSS-REFERENCE TO RELATED APPLICATION

This application claims the benefit of priority from U.S. Provisional Patent Application Ser. No. 62/993,728, filed on Mar. 24, 2020, and entitled "MANAGEMENT DEVICE FOR BAG-VALVE-MASK RESUSCITATORS," which is incorporated herein by reference in its entirety.

TECHNICAL FIELD

The present disclosure generally relates to resuscitators, particularly relates to manual resuscitators. More particularly, the present disclosure relates to systems and methods for controlling breathing parameters of a manual resuscitator, such as breathing rate, tidal volume, minute ventilation, breathing pace, and inspiratory to expiratory ratio.

BACKGROUND

Respiratory failure generally presents itself in the form of respiratory insufficiency or complete respiratory arrest. Acute respiratory failure may lead to high morbidity and mortality rate if not treated early. The mortality rate for people with acute respiratory failure is between 25 to 83% among in-hospital patients and even higher for out of hospital patients. The morbidity caused by acute respiratory failure is mainly due to low blood oxygenation, which may lead to extensive and irreversible destruction to brain, heart, and other organs.

Acute respiratory failure usually responds very well to early intervention. Patients who are treated early using artificial breathing devices have a high rate of survival and a good prognosis. In this regard, a simple manual breathing device is usually readily available to begin artificial breathing in an emergency. Bag-Valve-Mask devices are one of the most efficient and readily available manual breathing devices. Although bag-valve-masks have saved lives of many patients, it has recently been revealed that improper use of bag-valve-masks may lead to a high rate of mortality and morbidity as discussed in further detail below.

According to the latest guidelines of the American Heart Association (AHA), the artificial breathing rate is an important parameter determining the survival of patients with respiratory or cardio-respiratory arrest. The AHA has determined the optimum target rate of artificial breathing for adults with respiratory arrest as 10-12 breaths per minute. In addition, the breathing rate should be 2-10 breaths per minute for adults with cardiorespiratory arrest. The breathing rate differs for infants, children, and people with underlying diseases.

However, several studies have shown significant non-compliance between guideline recommendations and real practice. This non-compliance not only happens by the general public, or inexperienced members of the medical team but also by experienced medical personnel. For example, in one study it was revealed that even highly experienced paramedics were consistently ventilating cardiac arrested patients with breathing rates significantly higher than guidelines (i.e., hyperventilating patients). No rescuer in that study ventilated patients according to the guidelines, and they usually tended to ventilate patients with rates triple times or more than the recommended rates which substantially decreases the survival rates of the patients or causes irreversible life-long brain injuries.

The mechanism of the detrimental effect of hyperventilation during a respiratory arrest is partly understood. Hyperventilation contributes to increased intrathoracic pressure and may eventually lead to decreased heart coronary vessels' perfusion pressure, decreased cerebral perfusion pressure, induction of respiratory alkalosis, decreased cardiac output, loss of cerebrovascular autoregulation, brain cell hypoxemia, and initial and/or rebound increases in intracranial pressure in traumatic brain injury patients. The major problem is that all these detrimental effects are being inadvertently caused by medical teams and are not related to the main disease of a patient.

Previous attempts for preventing hyperventilation problem in bag-valve-masks were based on "educational methods", "systems for controlling breathing rate", and "cardiopulmonary resuscitation (CPR) metronomes". Despite educational training sessions, literature still shows the tendency of even experienced rescuers toward inappropriate hyperventilation. Researchers believe that some reasons that may cause rescuers to ignore the guidelines and hyperventilate patients are the high levels of stress in the setting of an emergency visit of a (cardio)pulmonary arrested patient, complex processes of resuscitation that may cause human error in counting the breathing, and an impacted mental state of a rescuer encountering unstable vital signs of an arrested patient despite extensive resuscitation efforts.

Efforts to develop systems for controlling breathing rate has led to the development of electronic control devices having sets of sensors being placed in the airway of bag-valve-masks and providing information via different types of displays. These electronic systems may include various sensors; such as pressure sensors, flow-rate sensors, oxygen sensors, carbon dioxide sensors, alcohol sensors, and sensors for detecting probable drugs in a patients' exhalation. These control devices may measure various respiratory parameters such as airflow rate, breathing rate, breathing air pressure, and other relevant parameters.

Since sensors of the prior art control devices are placed in an airway of a bag-valve-mask resuscitator, they need to be sterilized before being used for each patient, otherwise they may transmit diseases between patients. The sterilization could be accomplished by either making whole control device or at least the sensors single-use. However, this may lead to a significant increase in the price of a control device. Since bag-valve-masks are being largely used in prehospital and in-hospital emergencies, even a slight increase in their price due to new technology may face rejection by health system managers.

On the other hand, the whole control device or at least sensors of a control device may be made reusable. However, due to the sensitive electronic structures of these control devices, they cannot be autoclaved using common pressurized high-temperature water steam autoclaves. In this regard, they require advanced sterilization methods such as gamma-ray, plasma, or ethylene oxide sterilization. These methods are expensive and require specialized equipment, not readily available in many healthcare facilities. Apart from the method of sterilization, the collection, and processing of a large number of these control devices for sterilization require specific logistics which adds a burden to the already complex logistics of healthcare facilities.

It should also be noted that in routine practice, during the transfer of patients by ambulances, bag-valve-masks are usually moved along with patients into hospitals. Since ambulance units in many regions are independent of hospitals, management of the reusable control devices utilized in bag-valve-masks would be challenging. In one scenario, a control device may be transferred along with a bag-valve-mask and a patient to a hospital. However, returning such a large number of control devices to ambulance services would be a complex and costly practice.

In another scenario, a control device may be detached from a bag-valve-mask during the handover of a patient from an ambulance to a hospital. However, the detachment of an intra-airway sensor would require major manipulation of a bag-valve-mask and consequent pause of the breathing of a (cardio)respiratory arrested patient. There also needs to be another device (compatible with the type of the bag-valve-mask being used) to be connected to the bag-valve-mask at the hospital. This practice may be considered as an unnecessary interruption of the resuscitation of a critically ill patient and may even have legal consequences.

Apart from the aforementioned sterilization issue, most of the prior art control devices may require a completely new design for a manual resuscitation device. In this context, introducing a completely new resuscitation device would be challenging from various points of view, such as acquiring medical permissions, proving their efficacy, introduction of a new device to the healthcare systems, changing users' minds to accept them as a new standard for resuscitation procedures, educating a large number of people on how to use the new resuscitation devices, and amending regulatory guidelines to consider these new resuscitation devices as accepted systems for breathing.

Furthermore, producing such new resuscitation devices require a significant change in current production lines of manufacturers and the future state of current millions of bag-valve-masks in markets and healthcare systems is unknown. Therefore, although using prior art systems might improve the quality of patients' resuscitation, the costs of introducing them to the medical community may not justify their benefits.

As mentioned before, a CPR metronome may be utilized to prevent hyperventilation problem. A CPR metronome is basically a ticking clock that produces audio or visual indications. For example, to deliver 20 breaths per minute, a CPR metronome may tick every 3 seconds. A user who is performing an intervention such as a cardiac massage or resuscitation utilizing a manual resuscitator is supposed to perform a single massage or resuscitation with each indication made by an exemplary CPR metronome. However, if a user fails to do so, a CPR metronome cannot compensate for a missed intervention. In real practice, a resuscitation process may be far more complex and there is no guarantee that a user can adjust themselves with a CPR metronome indication. For example, while a CPR metronome is ticking, in a first exemplary scenario, a user may be engaged with tasks other than giving respiration. In a second exemplary scenario, a user may be stressed out due to unstable vital signs of an arrested patient and may be desperately delivering excess numbers of respirations. In the first exemplary scenario, a CPR metronome may not compensate for a missed breathing, and in the second exemplary scenario a CPR metronome may not produce an alarm for a user to stop hyperventilating. Furthermore, a CPR metronome may not be capable of evaluate quality of given ventilations. In an exemplary scenario, a user may not adequately squeeze the bag due to being tired of performing CPR for a while. In this exemplary scenario, a CPR metronome may not detect an improperly delivered breathing.

There is, therefore, a need for a simple and cost-effective control device that may be utilized in a currently available bag-valve-mask resuscitator without being installed in an airway of such bag-valve-mask resuscitator. There is further a need for a device that may evaluate quality and quantity of resuscitation breathings and provide real-time guidance to a user or a caregiver to achieve proper resuscitation parameters.

SUMMARY

This summary is intended to provide an overview of the subject matter of the present disclosure and is not intended to identify essential elements or key elements of the subject matter, nor is it intended to be used to determine the scope of the claimed implementations. The proper scope of the present disclosure may be ascertained from the claims set forth below in view of the detailed description and the drawings.

According to one or more exemplary embodiments, the present disclosure is directed to a resuscitation management system for a manual resuscitator. An exemplary system may include a first accelerometer that may be configured to be mounted on a first side of an outer surface of a resuscitation bag of an exemplary manual resuscitator. An exemplary first accelerometer may be configured to measure a first acceleration vector for an exemplary first side. An exemplary first acceleration vector may include a first acceleration magnitude as a function of time and a first spatial direction of acceleration.

An exemplary system may further include a second accelerometer that may be configured to be mounted on a second side of an exemplary outer surface of a resuscitation bag of an exemplary manual resuscitator. An exemplary second accelerometer may be configured to measure a second acceleration vector for an exemplary second side. An exemplary second acceleration vector may include a second acceleration magnitude as a function of time and a second spatial direction of acceleration. An exemplary second side may be opposite an exemplary first side along a first axis perpendicular to a longitudinal axis of an exemplary resuscitation bag.

An exemplary system may further include a processing unit that may be coupled to an exemplary first accelerometer and an exemplary second accelerometer. An exemplary processing unit may include at least one processor, and at least one memory that may be coupled to at least one exemplary processor. At least one exemplary memory may store executable instructions to urge at least one exemplary processor to receive an exemplary first acceleration vector from an exemplary first accelerometer, receive an exemplary second acceleration vector from an exemplary second accelerometer, and obtain a resultant acceleration vector by subtracting an exemplary second acceleration vector from an exemplary first acceleration vector. An exemplary resultant acceleration vector may include an acceleration magnitude as a function of time and a spatial acceleration direction. At least one exemplary memory may store further executable instructions to urge at least one exemplary processor to calculate a speed of compression/decompression of an exemplary resuscitation bag as a function of time for a time interval by integrating the acceleration magnitude as a function of time over an exemplary time interval, and calculate an extent of compression/decompression of an exemplary resuscitation bag as a function of time for the time interval by integrating the speed of compression/decompression as a function of time over an exemplary time interval.

BRIEF DESCRIPTION OF THE DRAWINGS

The novel features which are believed to be characteristic of the present disclosure, as to its structure, organization, use and method of operation, together with further objectives and advantages thereof, will be better understood from the following drawings in which a presently exemplary embodiment of the present disclosure will now be illustrated by way of example. It is expressly understood, however, that the drawings are for illustration and description only and are not intended as a definition of the limits of the present disclosure. Embodiments of the present disclosure will now be described by way of example in association with the accompanying drawings in which.

DETAILED DESCRIPTION

Figure 1A:
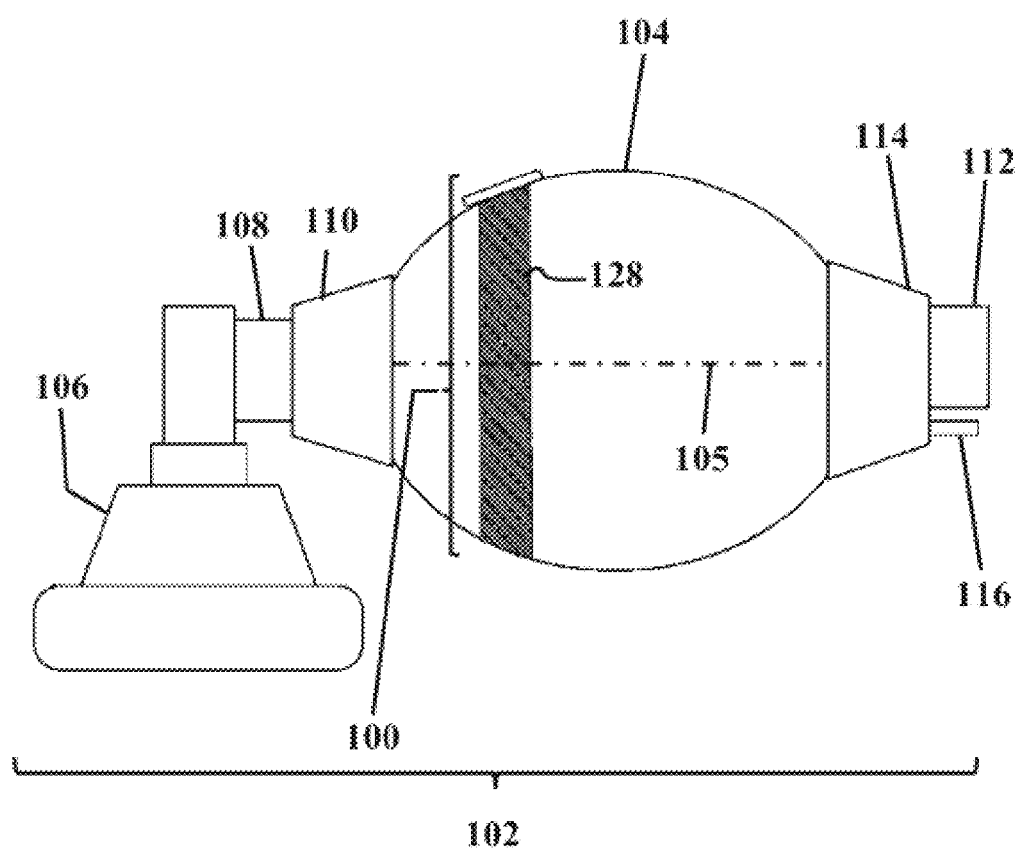
FIG. 1A illustrates a schematic side-view of a resuscitation management device mounted on a manual resuscitator, consistent with one or more exemplary embodiments of the present disclosure.

The novel features which are believed to be characteristic of the present disclosure, as to its structure, organization, use and method of operation, together with further objectives and advantages thereof, will be better understood from the following discussion.

The present disclosure is directed to exemplary embodiments of a system and method for resuscitation management that may be used for a manual resuscitator. An exemplary resuscitation management system may detect compression of a bag of a manual resuscitator and may associate each detected compression of the bag with a single breath delivered to a patient. An exemplary resuscitation management system may further generate an indication signal so as to provide information related to a breathing rate of a patient to a user. Such information may guide a user to achieve a target breathing rate. In an exemplary embodiment, achieving the target breathing rate may impact the survival chance of a patient and may prevent damages related to improper ventilation of a patient, such as brain damages. A user may be a rescuer or a caregiver who is utilizing a manual resuscitator to help a patient breathe. As used herein, air, gas, and breathing gases may be used interchangeably and may refer to gaseous materials that a person may inhale or exhale for the purpose of respiration and may either include a single chemical element or a combination of various chemical elements.

An exemplary resuscitation management system may include a sensor assembly that may be configured to detect a state of a resuscitation bag between a compressed state and a decompressed state. An exemplary sensor assembly may further be configured to detect an extent of compression of an exemplary resuscitation bag at any given moment during a resuscitation procedure. An exemplary resuscitation management system may be configured to receive a detected state of an exemplary resuscitation bag and data regarding the extent of compression of an exemplary resuscitation bag from an exemplary sensor assembly and associate each adequate compression of an exemplary resuscitation bag with a ventilation delivered to a patient. An exemplary adequate compression of an exemplary resuscitation bag may correspond to an extent of compression of an exemplary resuscitation bag that may allow for pushing out an adequate volume of breathing gases out of an exemplary resuscitation bag. An exemplary adequate volume of breathing gases may be determined based on the age, type, and medical condition of a patient.

An exemplary sensor assembly may include at least one of a flex sensor, an accelerometer, a pressure/tension sensor, and a push button. An exemplary sensor assembly may be configured to generate an output signal indicative of a state of an exemplary resuscitation bag between a decompressed state and a compressed state, an extent of compression of an exemplary resuscitation bag, and a speed at which an exemplary state of an exemplary resuscitation bag changes between an exemplary decompressed state and an exemplary compressed state.

An exemplary resuscitation management system may further include a processing unit that may be coupled with an exemplary sensor assembly. An exemplary processing unit may be configured to receive an exemplary output signal from an exemplary sensor assembly and calculate breathing parameters such as a breathing rate, a minute ventilation, a tidal volume, and an inspiratory to expiratory time (I:E) ratio, based at least in part on an exemplary output signal or a plurality of exemplary output signals received form an exemplary sensor assembly. In other words, an exemplary processing unit may be configured to calculate breathing parameters such as a breathing rate, a minute ventilation, a tidal volume, and an I:E ratio, based at least in part on at least one of number of compressions in a given time interval, extent of each compression performed during a given time interval, and a speed at which an exemplary resuscitation bag is compressed.

An exemplary sensor assembly may be mounted on an outer surface of an exemplary resuscitation bag without any contact with contents of the bag. Such isolation of breathing gases from an exemplary sensor assembly may eliminate risks of improper sterilization of a sensor assembly. In practice, no contamination may enter a flow of breathing gas from an exemplary sensing assembly since there is no contact between the breathing gases and an exemplary sensor assembly. Furthermore, an exemplary sensor assembly mounted on an outer surface of a resuscitating bag may allow for an easy and quick removal or change of an exemplary sensor assembly, which may be beneficial from a practical standpoint. For example, an exemplary resuscitation management device may be mounted around an outer surface of an exemplary resuscitation bag by utilizing a flexible band. Such utilization of an exemplary flexible band to mount an exemplary resuscitation management device on an exemplary resuscitation bag may allow for easily and quickly mounting an exemplary resuscitation management device on resuscitation bags of various sizes. Furthermore, such flexible band mount may allow for easily and quickly removing an exemplary resuscitation management device by simply taking off an exemplary flexible band from around an exemplary resuscitation bag. In an exemplary scenario, such easy and quick removal of an exemplary resuscitation management device may be beneficial when an ambulance crew are handing over a (cardio)respiratory arrested patient to a hospital crew and need to quickly unmount their exemplary resuscitation management device from an exemplary resuscitation bag.

In an exemplary embodiment, an exemplary sensor assembly may include at least one flex sensor that may be mounted on an outer surface of an exemplary resuscitation bag. An exemplary flex sensor may be configured to sense a state of an exemplary resuscitation bag between a decompressed state and a compressed state based at least in part on an extent of bending of an exemplary flex sensor. An exemplary flex sensor may be bent at a first angle in an exemplary decompressed state of an exemplary resuscitation bag and at a second angle in an exemplary compressed state of an exemplary resuscitation bag. Consequently, an exemplary flex sensor may be configured to determine a state and an extent of compression of an exemplary bag based at least in part on the angle of an exemplary flex sensor at any given instance. An exemplary flex sensor may further be configured to calculate a compression speed of an exemplary resuscitation bag based on detected amount of change in the angle of an exemplary flex sensor for a given time interval.

In an exemplary embodiment, an exemplary sensor assembly may further include at least one accelerometer that may be mounted on an outer surface of an exemplary resuscitation bag. An exemplary accelerometer may be configured to sense a state of an exemplary resuscitation bag between a decompressed state and a compressed state based at least in part on an amount of acceleration/deceleration sensed by an exemplary accelerometer during a change in an exemplary state of an exemplary resuscitation bag between a decompressed state and a compressed state. An exemplary accelerometer may further be configured to sense a state of an exemplary resuscitation bag between a decompressed state and a compressed state based at least in part on a sensed spatial direction of an acceleration/deceleration sensed by an exemplary accelerometer during a change in an exemplary state of an exemplary resuscitation bag between a decompressed state and a compressed state. In practice, when a user compresses an exemplary resuscitation bag, an outer surface of an exemplary resuscitation bag may be pushed inward and when a user releases an exemplary resuscitation bag, an exemplary outer surface of an exemplary resuscitation bag may move outward to go back to an initial position of an exemplary outer surface. Such inward and outward motion of an exemplary outer surface of an exemplary resuscitation bag may be sensed by sensing an amount of acceleration/deceleration of an exemplary point on an exemplary outer surface and a spatial direction of such acceleration/deceleration. In other words, an exemplary accelerometer may be configured to generate an output signal indicative of a state and extent of compression of an exemplary resuscitation bag based at least in part on sensed amounts of acceleration/decelerations of an exemplary outer surface of an exemplary resuscitation bag during a compression/decompression movement or deformation of an exemplary outer surface and further based on sensed spatial directions of movement of an exemplary outer surface of an exemplary resuscitation bag.

In an exemplary embodiment, an exemplary sensor assembly may further include at least one pressure/tension sensor that may be mounted on an outer surface of an exemplary resuscitation bag. An exemplary pressure/tension sensor may be configured to sense a state of an exemplary resuscitation bag between a decompressed state and a compressed state based at least in part on an amount of pressure exerted by a user's hand on an exemplary resuscitation bag during compression of an exemplary resuscitation bag. An exemplary pressure/tension sensor may be mounted on an exemplary resuscitation bag such that a user may press on an exemplary pressure/tension sensor to compress an exemplary resuscitation bag. An exemplary pressure/tension sensor may be configured to generate an output signal indicative of at least the amount of pressure sensed. An exemplary processing unit may then receive the output signal of an exemplary pressure/tension sensor and may utilize a calibration data to associate the amount of pressure with a state of compression of an exemplary resuscitation bag.

In an exemplary embodiment, an exemplary sensor assembly may further include at least one push button that may be mounted on an outer surface of an exemplary resuscitation bag. An exemplary push button may be configured to determine if an exemplary resuscitation bag is compressed by closing a circuit when an amount of pressure exerted on an exemplary push button exceeds a predetermined threshold.

As mentioned before, such implementation of an exemplary sensor assembly that may be mounted on an outer surface of an exemplary resuscitation bag may allow for determining the compression/decompression of an exemplary resuscitation bag and then utilizing the determined compression/decompression state of an exemplary resuscitation bag by an exemplary processing unit to calculate breathing parameters, such as breathing rates. An exemplary resuscitation management system and device may utilize such calculated breathing parameters to help a user deliver correct amount of ventilation to a patient at appropriate time intervals so that any risks of hyperventilation or hypoventilation may be avoided.

Figure 1B:
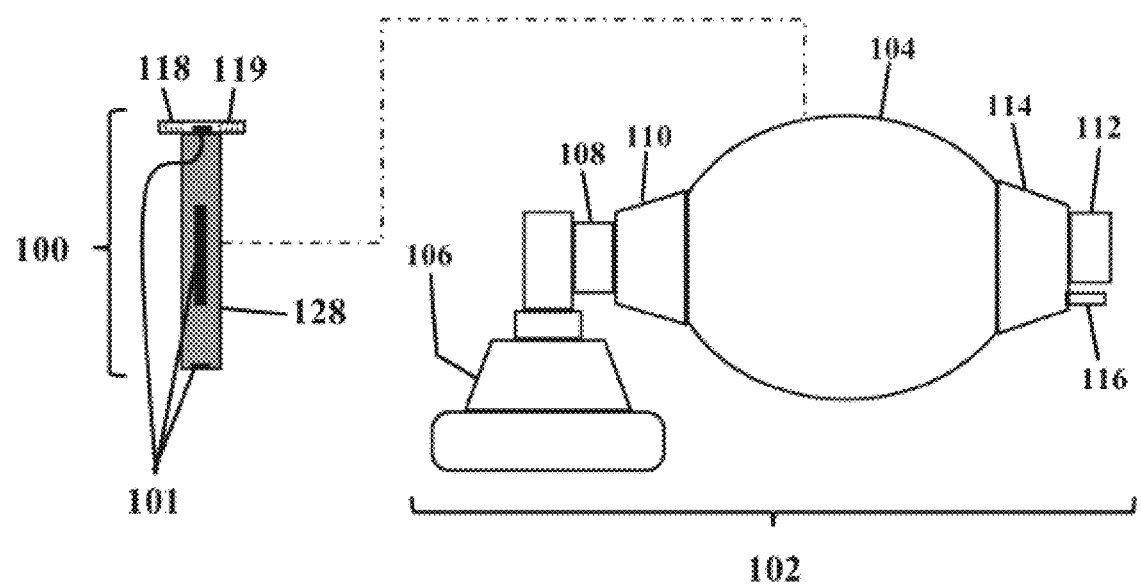
FIG. 1B illustrates a schematic exploded side-view of a resuscitation management device mounted on a manual resuscitator, consistent with one or more exemplary embodiments of the present disclosure.

FIG. 1A illustrates a schematic side-view of a resuscitation management device 100 mounted on a manual resuscitator 102, consistent with one or more exemplary embodiments of the present disclosure. FIG. 1B illustrates a schematic exploded side-view of resuscitation management device 100 mounted on manual resuscitator 102, consistent with one or more exemplary embodiments of the present disclosure. In an exemplary embodiment, manual resuscitator 102 may include a bag-valve-mask resuscitator, which may include a bag 104 that may be connected to a mask 106 via an anterior flow channel 108. In an exemplary embodiment, mask 106 may be placed on the nose and/or mouth of a patient (not illustrated) and may provide a sealed connection between a patient's airway and bag 104. In an exemplary embodiment, air or other breathing gases, such as oxygen may be manually pumped into a patient's airway by manually compressing and decompressing bag 104, which may be an inflatable or a self-inflatable bag. In an exemplary embodiment, manual resuscitator 102 may further include an anterior valve assembly 110 connected between bag 104 and mask 106 on anterior flow channel 108. In an exemplary embodiment, anterior valve assembly 110 may include a diaphragmatic or a shutter valve that may allow air or other breathing gases to pass through anterior flow channel 108 from bag 104 to mask 106 and may further divert exhaled breath of a patient to the atmosphere.

In an exemplary embodiment, bag 104 may receive air or other breathing gases from a posterior flow channel 112 that may be connected to bag 104 via a posterior valve assembly 114. In an exemplary embodiment, posterior valve assembly 114 may include a diaphragmatic or a shutter valve that may be a one-way valve allowing air or other breathing gases into bag 104. In an exemplary embodiment, a reservoir bag (not illustrated) may further be connected to posterior flow channel 112 and may provide a large volume of air or other breathing gases to bag 104 via posterior valve assembly 114. As mentioned before, in an exemplary embodiment, a user, such as a rescuer or a caregiver may squeeze bag 104 to deliver air or other breathing gases to a patient via mask 106. When bag 104 is released by a user, bag 104 may be decompressed or self-inflated and fresh air or other breathing gases may refill bag 104 either through posterior flow channel 112 or other inlet tubes, such as inlet tube 116.

In an exemplary embodiment, manual resuscitator 102 may include any other type of patient airway interface other than mask 106, for example, an endotracheal tube or a laryngeal mask may further be used instead of mask 106. As used herein, a patient airway interface may refer to any kind of device that may connect manual resuscitator 102 to a patient's airway.

In an exemplary embodiment, each time bag 104 is squeezed by a user, one positive pressure flow of a breathing gas may be provided to a patient and may be counted as a single respiration or breath. In an exemplary embodiment, bag 104 may be squeezable or compressible by a user along axes perpendicular to a longitudinal axis 105 of bag 104. In an exemplary embodiment, longitudinal axis 105 may be an axis associated with the longest dimension of bag 104. For example, longitudinal axis 105 may extend along bag 104 between anterior valve assembly 110 and posterior valve assembly 114. As used herein, a positive pressure flow of air, a respiration, a breath, and an adequate ventilation delivered to a patient may be used interchangeably and may refer to delivering an adequate volume of breathing gases into a patient's lungs.

In an exemplary embodiment, manual resuscitator 102 may be of different sizes to fit different age groups, such as infants, children, and adults. For each age group, a proper range of breathing rate, inspiratory time to expiratory time (I:E) ratio, tidal volume, and minute ventilation should be provided to a patient, where such proper breathing rate, I:E ratio, tidal volume, or minute ventilation, are referred to herein as a target breathing rate, a target I:E ratio, a target tidal volume, or a target minute ventilation, respectively. As used herein, a breathing rate range may refer to a number of respirations or breaths provided by manual resuscitator 102 per minute or other reference time periods. For example, 10 to 12 respirations per minute in an adult and 12 to 20 respirations per minute in a child may be considered as a target respiratory or breathing rate range.

In an exemplary embodiment, I:E ratio may refer to the ratio between an inspiratory time and an expiratory time. For example, I:E ratio of 1:2 to 1:3 in an adult, or I:E ratio of 1:1.5 to 1:2 in an infant may be considered as a target I:E ratio. In an exemplary embodiment, tidal volume may refer to a volume of air delivered to lungs of a patient with each breath by an exemplary manual resuscitator. For example, a tidal volume of 500 to 600 ml in an adult, or a tidal volume of 100 to 200 ml in a child may be considered as a target tidal volume. In an exemplary embodiment, a minute ventilation may refer to a volume of gas inhaled or exhaled from a person's lungs per minute, or a volume of air delivered to lungs of a patient by an exemplary manual resuscitator per minute. For example, a minute ventilation of 5 to 8 liter in an adult, or a minute ventilation of 240 to 360 mL/kg in a child may be considered as a target minute ventilation.

In an exemplary embodiment, resuscitation management device 100 that may be mounted on an outer surface of bag 104 of manual resuscitator 102, may be configured to manage at least one of a respiration or breathing rate, an I:E ratio, a tidal volume, or a minute ventilation that may be provided by a user to a patient by utilizing manual resuscitator 102. In other words, resuscitation management device 100 may help a user to deliver at least one of a target respiratory or breathing rate, a target I:E ratio, a target tidal volume, or a target minute ventilation to a patient, based at least in part on age group and medical condition of that patient. To this end, in an exemplary embodiment, resuscitation management device 100 may be configured to calculate at least one of a respiration rate or breathing rate, or an I:E ratio by counting the number of times and measuring the speed at which bag 104 is compressed by a user, and calculate at least one of a tidal volume, or a minute ventilation by measuring the extent of compression of bag 104 by a user, and then based at least in part on one of the calculated breathing rate, the calculated I:E ratio, the calculated tidal volume, or the calculated minute ventilation may provide a user with audio, visual, tactile, or mechanical guidelines as to how to proceed with the resuscitation process.

In an exemplary embodiment, resuscitation management device 100 may include a sensor assembly 101 that may be mounted on an outer surface of bag 104 of manual resuscitator 102. In an exemplary embodiment, sensor assembly 101 may include at least one of a flex sensor, an accelerometer, a pressure/tension sensor, and a push button. In an exemplary embodiment, resuscitation management device 100 may further include a processing unit 118 and an input/output (I/O) interface 119 that may be coupled with sensor assembly 101. In an exemplary embodiment, resuscitation management device 100 may further include a flexible band 128, on which sensor assembly 101, processing unit 118, and I/O interface 119 may be attached. In an exemplary embodiment, flexible band 128 may be wearable around bag 104, such that sensor assembly 101 may be positioned on an outer surface of bag 104. In an exemplary embodiment, sensor assembly 101 may be attached on an inner side of flexible band 128 or an outer side of flexible band 128. In an exemplary embodiment, flexible band 128 may be made of two outer layers and sensor assembly 101 may be positioned between the two outer layers.

Figure 2:
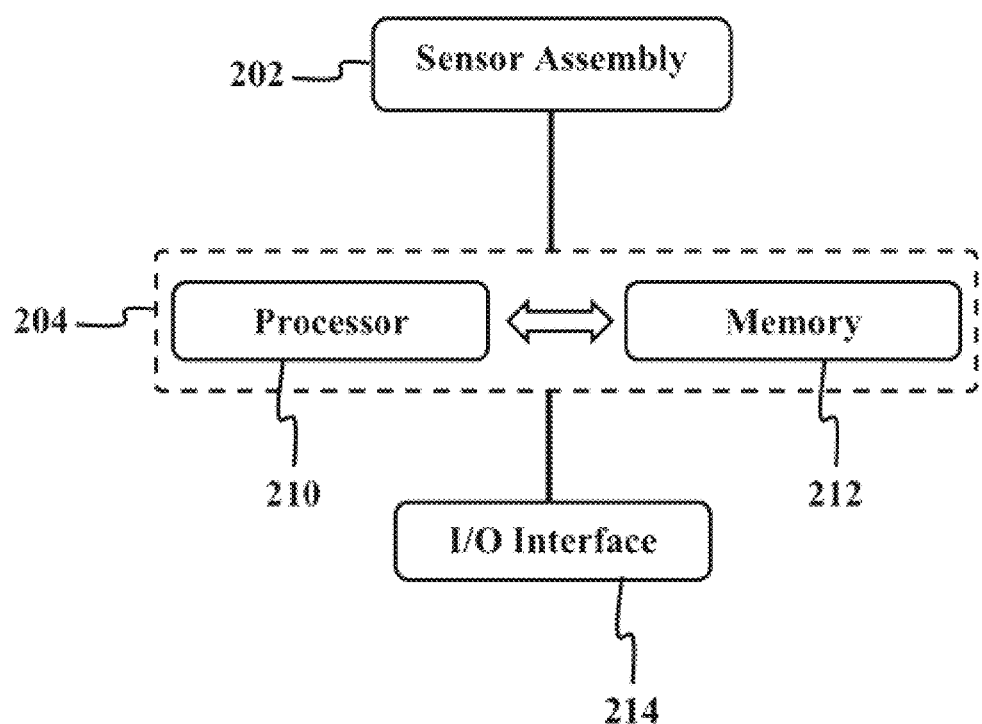
FIG. 2 illustrates a functional block diagram of a resuscitation management system, consistent with one or more exemplary embodiments of the present disclosure.

FIG. 2 illustrates a functional block diagram of a resuscitation management system 200, consistent with one or more exemplary embodiments of the present disclosure. In an exemplary embodiment, resuscitation management system 200 may be similar to resuscitation management device 100 and may include a sensor assembly 202 and a processing unit 204 that may be coupled to sensor assembly 202. In an exemplary embodiment, sensor assembly 202 may be similar to sensor assembly 101 and may include at least one of a flex sensor, a pressure/tension sensor, an accelerometer, and a push button. As mentioned before, in an exemplary embodiment, sensor assembly 202 may be configured to generate an output signal indicative of an extent of compression of a resuscitation bag at any given moment. In an exemplary embodiment, processing unit 204 may include a processor 210 and a memory 212 that may be coupled to processor 210. In an exemplary embodiment, memory 212 may store executable instructions to urge processor 210 to receive a plurality of output signals from sensor assembly 202, determine an extent of compression of a resuscitation bag at a given instance based on the received output signal at the given instance, associate a compression of a resuscitation bag with an adequate ventilation delivered to a patient responsive to the determined extent of compression of the resuscitation bag exceeding a predetermined threshold. In an exemplary embodiment, the predetermined threshold may correspond to a 90±10% of the resuscitation bag being compressed, such that a volume of breathing gas equal to 90±10% of an internal volume of the resuscitation bag may be pushed out of the resuscitation bag. In an exemplary embodiment, memory 212 may store further executable instructions to urge processor 210 to calculate a breathing rate by counting the adequate ventilations delivered to in one minute or any other reference times.

In an exemplary embodiment, memory 212 may store further executable instructions to urge processor 210 to calculate a speed of compression of the resuscitation bag based on the amount of change in the compression extent of the resuscitation bag over time and calculate an I:E ratio based at least in part on the calculated speed of compression of the resuscitation bag. In an exemplary embodiment, memory 212 may store further executable instructions to urge processor 210 to calculate a volume of breathing gases delivered to a patient in a single compression of the resuscitation bag (tidal volume) based at least in part on the determined extent of compression of the resuscitation bag. In an exemplary embodiment, memory 212 may store further executable instructions to urge processor 210 to calculate a minute ventilation based at least in part on the calculated breathing rate and calculated volume of breathing gases delivered to a patient in a single compression of the resuscitation bag.

In an exemplary embodiment, resuscitation management system 200 may further include an input/output (I/O) interface 214 that may further be coupled to processing unit 204. In an exemplary embodiment, memory 212 may further store executable instructions to urge processor 210 to provide information on I/O interface 214 based at least in part on at least one of the calculated breathing rate, the calculated I:E ratio, the calculated tidal volume, and the calculated minute ventilation. In an exemplary embodiment, I/O interface 214 may include a display, where the information provided on the display may include one or a combination of numbers representing the calculated breath rate and target breathing rate. In an exemplary embodiment, the information provided on the display may further include the calculated I:E ratio and the target I:E ratio, the calculated tidal volume and the target tidal volume, or the calculated minute ventilation and the target minute ventilation, alarm notifications, and a timeline showing the past, and upcoming breathing timepoints according to the calculated breathing rate.

In an exemplary embodiment, the I/O interface may include an alarm that may be configured to produce a plurality of one or more audio, visual, tactile, or mechanical indications. In an exemplary embodiment, memory 212 may further store a target breathing rate range and executable instructions to urge processor 210 to compare the calculated breathing rate and the target breathing rate range, urge the alarm to produce at least one of a first audio indication, a first visual indication, a first tactile indication, and a first mechanical indication responsive to the calculated breathing rate being in the target breathing rate range, and urge the alarm to produce at least one of a second audio indication, a second visual indication, a second tactile indication, and a second mechanical indication responsive to the calculated breathing rate being outside the target breathing rate range.

In an exemplary embodiment, memory 212 may further store a plurality of target breathing rate ranges, where each breathing rate range of the plurality of target breathing rate ranges may be associated with an age group. I/O interface 214 may further be configured to receive data from a user, where the data may include at least one of a user-defined target breathing rate, age group, medical condition of patient, and a patient type (human or animal). In an exemplary embodiment, memory 212 may further store executable instructions to urge processor 210 to select a breathing rate range based on the received data from the user, compare the calculated breathing rate and the selected target breathing rate range, urge the alarm to produce at least one of a first audio indication, a first visual indication, a first tactile indication, and a first mechanical indication responsive to the calculated breathing rate being in the selected target breathing rate range, and urge the alarm to produce at least one of a second audio indication, a second visual indication, a second tactile indication, and a second mechanical indication responsive to the calculated breathing rate being outside the selected target breathing rate range.

In an exemplary embodiment, memory 212 may further store a target I:E ratio, a target tidal volume or a target minute ventilation associated with various patient types (human or animal), age groups, and medical conditions. In an exemplary embodiment, memory 212 may further store executable instructions to urge processor 210 to select at least one of a target I:E ratio, a target tidal volume, and a target minute ventilation based at least in part on at least one of the received age group, the patient type, and the medical condition of a patient, calculate at least one of an I:E ratio, a tidal volume, a minute ventilation based on the received output signals from sensor assembly 202, compare at least one of the calculated I:E ratio, the calculated tidal volume, the calculated minute ventilation with the selected target values of I:E ratio, tidal volume, minute ventilation, and urge the alarm to produce at least one of an audio indication, a visual indication, a tactile indication, and a mechanical indication responsive to the calculated values being within selected target range or not.

Figure 3A:
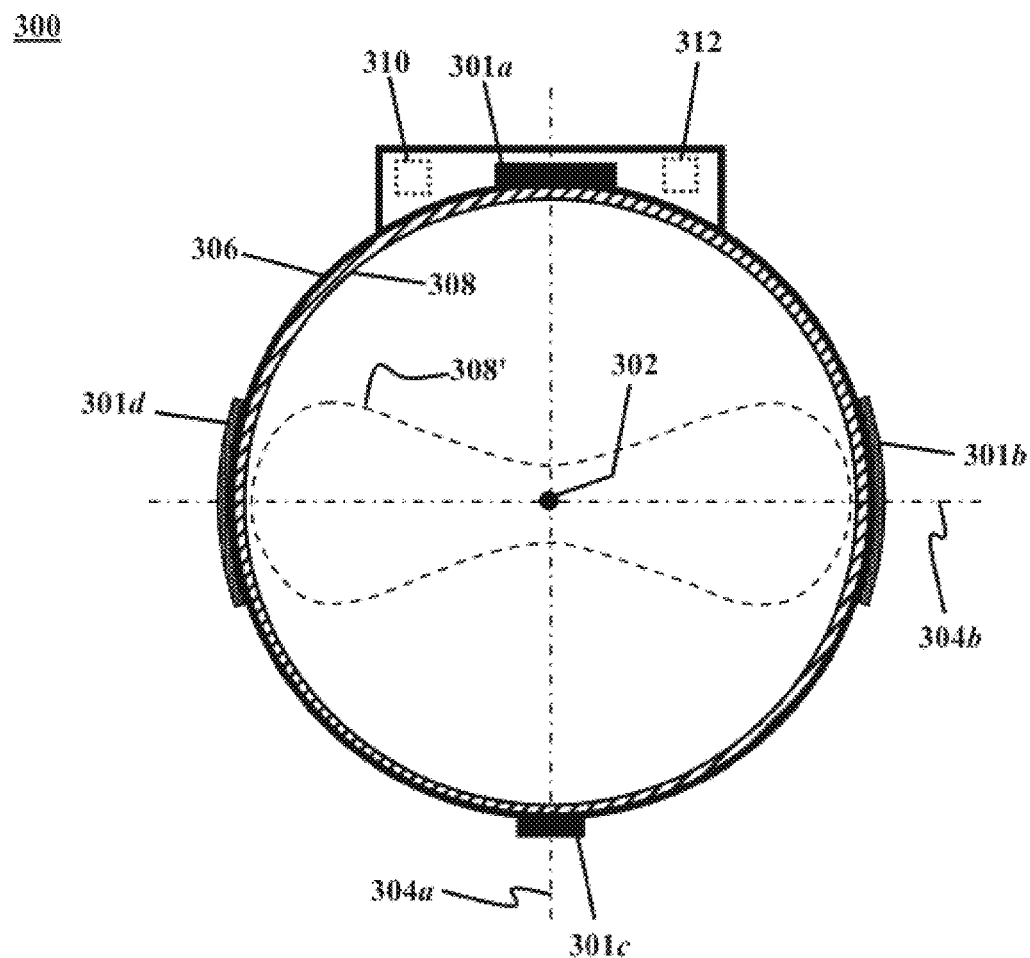
FIG. 3A illustrates a schematic front view of a resuscitation management device mounted around a resuscitation bag, consistent with one or more exemplary embodiments of the present disclosure.

FIG. 3A illustrates a schematic front view of a resuscitation management device 300 mounted around a resuscitation bag 308, consistent with one or more exemplary embodiments of the present disclosure. Referring to FIG. 3A, reference numeral 300 refers to a resuscitation management device that includes all illustrated elements except for the resuscitation bag 308, which is referred to by reference numeral 308. In an exemplary embodiment, resuscitation management device 300 may be similar to resuscitation management device 100 and resuscitation bag 308 may be similar to bag 104.

In an exemplary embodiment, resuscitation management device 300 may include a sensor assembly similar to sensor assembly 202 that may include a plurality of sensors (301a-301d) that may be attached to a flexible band 306 similar to flexible band 128. In an exemplary embodiment, resuscitation management device 300 may further include a processing unit 310 similar to processing unit 204 and an I/O interface 312 similar to I/O interface 214. In an exemplary embodiment, processing unit 310 and I/O interface 312 may also be mounted on or attached to flexible band 306. In an exemplary embodiment, flexible band 306 may be mounted around resuscitation bag 308, such that plurality of sensors (301a-301d) may be positioned on an outer surface of resuscitation bag 308. In an exemplary embodiment, flexible band 306 may be mounted around resuscitation bag 308 to form a round enclosure around resuscitation bag 308 with a plane of the round enclosure perpendicular to a longitudinal axis 302 of resuscitation bag 308. As illustrated in FIG. 3A, longitudinal axis 302 of resuscitation bag 308 is perpendicular to the view.

In an exemplary embodiment, as mentioned before, resuscitation bag 308 may be squeezed or compressed by a user along axes perpendicular to longitudinal axis 302 of resuscitation bag 308. For example, resuscitation bag 208 may be squeezed or compressed along axis 304a, axis 304b, or any similar axis perpendicular to longitudinal axis 302. For example, resuscitation bag 308 may be compressed along axis 304a to a compressed state 308'. In an exemplary embodiment, sensors (301a-301d) may be positioned on the outer surface of resuscitation bag 308 along such axes that are perpendicular to longitudinal axis 302. For example, sensors 301a and 301c may be mounted along axis 304a and sensors 301b and 301d may be mounted along axis 304b. In an exemplary embodiment, each sensor of plurality of sensors (301a-301d) may include one of a flex sensor, an accelerometer, a pressure/tension sensor, and a push button. In an exemplary embodiment, sensors (301a-301d) may be similar or of different types.

Figure 3B:
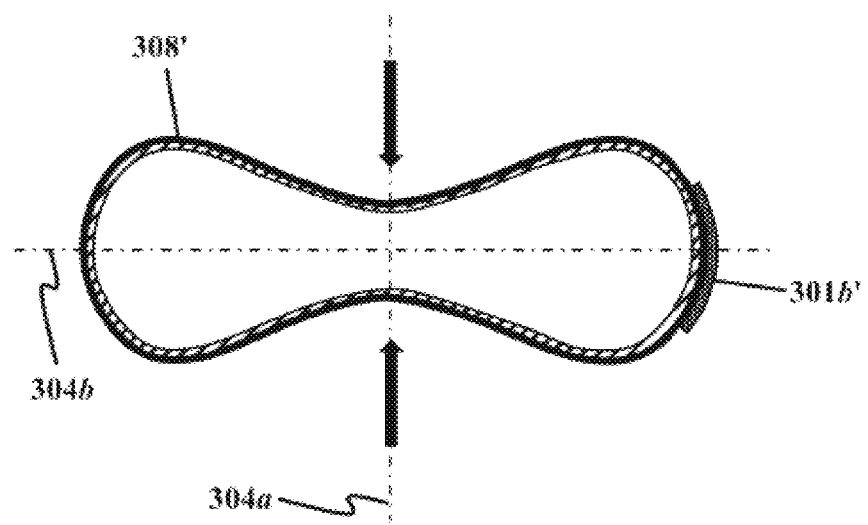
FIG. 3B illustrates a schematic sectional side-view of a compressed resuscitation bag, consistent with one or more exemplary embodiments of the present disclosure.

FIG. 3B illustrates a schematic sectional front-view of a compressed resuscitation bag 308', consistent with one or more exemplary embodiments of the present disclosure. In an exemplary embodiment, sensor 301b' may be sensor 301b which is bent in response to the compression of resuscitation bag 308. In an exemplary embodiment, sensor 301b may be a flex sensor mounted along an axis perpendicular to an axis along which resuscitation bag 308 is to be compressed. For example, sensor 301b may be mounted along axis 304b and resuscitation bag 308 may be compressed along axis 304a. In an exemplary embodiment, sensor 301b may be bent to a bent state (referred to herein as bent sensor 301b') in response to resuscitation bag 308 being compressed to a compressed state (referred to herein as compressed resuscitation bag 308'). In an exemplary embodiment, sensor 301b that may be a flex sensor may be configured to generate an output signal responsive to an extent to which the flex sensor is bent. An exemplary extent to which an exemplary flex sensor is bent may be determined based on a bend angle of an exemplary flex sensor.

Figure 4:
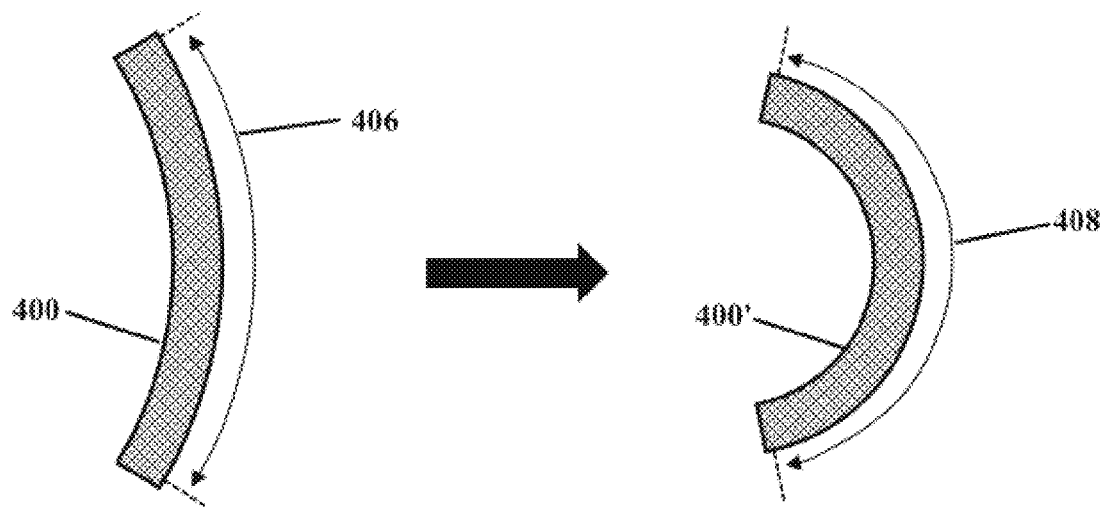
FIG. 4 illustrates a schematic representation of a flex sensor and a bent flex sensor state, consistent with one or more exemplary embodiments of the present disclosure.

FIG. 4 illustrates a schematic representation of a flex sensor 400 and a bent flex sensor state 400', consistent with one or more exemplary embodiments of the present disclosure. In an exemplary embodiment, flex sensor 400 refers to an exemplary flex sensor mounted on resuscitation bag 308 and bent flex sensor 400' refers to the flex sensor that may have bent due to compression of resuscitation bag 308 to a compressed state designated by 308'. In an exemplary embodiment, flex sensor 400 may be similar to sensor 301b and bent flex sensor 400' may be similar to sensor 301b'. In an exemplary embodiment, flex sensor 400' may simply refer to flex sensor 400 in a bent state.

In an exemplary embodiment, flex sensor 400 may have a first bend angle 406 and bent flex sensor 400' may have a second bend angle 408. In an exemplary embodiment, an exemplary flex sensor may be structures as an elongated band that may be attached to an outer surface of resuscitation bag 308. In an exemplary embodiment, flex sensor 400 may conform to the shape of the outer surface of decompressed resuscitation bag 308 and may have a bend angle equal to first bend angle 406. In an exemplary embodiment, bent flex sensor 400' may be bent in response to the outer surface of resuscitation bag 308 being bent due to the compression of resuscitation bag 308. In other words, bent flex sensor 400' may conform to the shape of the outer surface of compressed resuscitation bag 308' and may have a bend angle equal to second bend angle 408.

In an exemplary embodiment, an exemplary flex sensor may be configured to generate an output signal corresponding to a bend angle of an exemplary flex sensor. For example, an exemplary flex sensor may be configured to generate a first output signal corresponding to an exemplary flex sensor being bent at first bend angle 406 and to generate a second output signal corresponding to an exemplary flex sensor being bent at a second bend angle 408. In an exemplary embodiment, an exemplary flex sensor may be configured to generate a plurality of output signals responsive to an exemplary flex sensor being bent between first bend angle 406 and second bend angle 408. Each output signal of the plurality of output signals may correspond to a bending extent of an exemplary flex sensor at a given moment during bending of an exemplary flex sensor between first bend angle 406 and second bend angle 408. In an exemplary embodiment, a rate at which a bend angle of an exemplary flex sensor changes between first bend angle 406 and second bend angle 408 in a given time interval may correspond to a speed of compression of an exemplary resuscitation bag. Furthermore, in an exemplary embodiment, bending extent of an exemplary flex sensor may be calibrated and correlated with a compression extent of an exemplary manual resuscitation bag.

In an exemplary embodiment, sensor assembly 202 may include a flex sensor that may be configured to generate an output signal indicating an extent of bending of an exemplary flex sensor. In an exemplary embodiment, memory 212 may store a calibration curve or a look up table that may correlate an extent of bending of sensor assembly 202 with an extent of compression of a resuscitation bag at any given moment. In an exemplary embodiment, memory 212 may include executable instructions to urge processor 210 to receive a plurality of output signals generated by sensor assembly 202 for a time interval, associate each output signal of the plurality of output signals at a given moment to an extent of compression of the resuscitation bag at the given moment utilizing the stored calibration curve or the look up table.

Figure 5A:
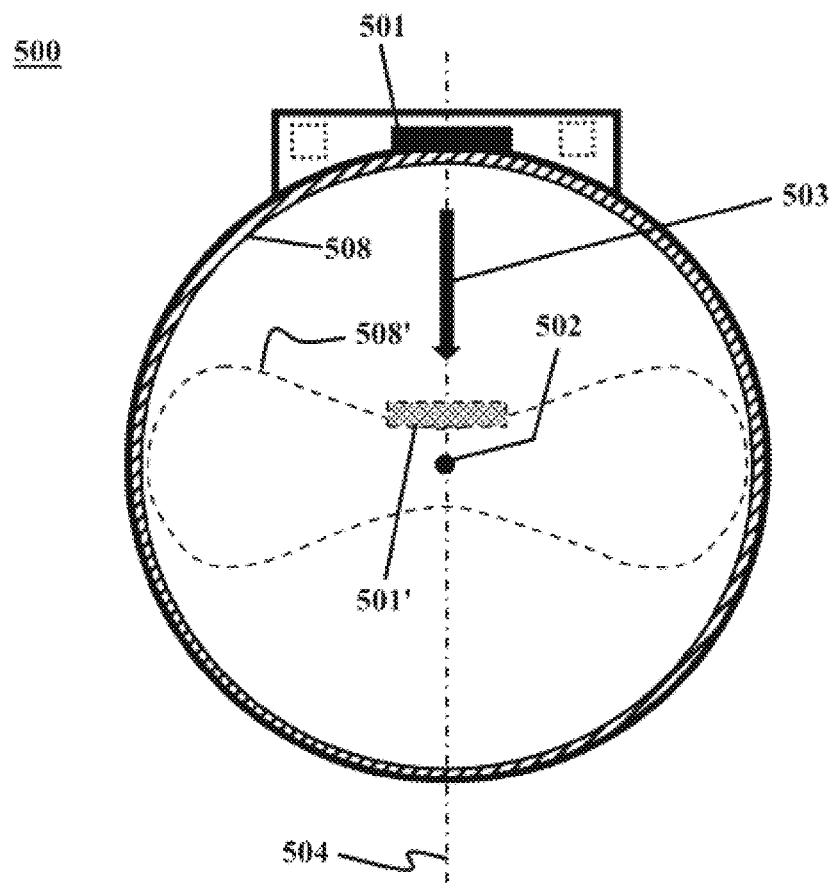
FIG. 5A illustrates a schematic front view of a resuscitation management device mounted around a resuscitation bag, consistent with one or more exemplary embodiments of the present disclosure.

FIG. 5A illustrates a schematic front view of a resuscitation management device 500 mounted around a resuscitation bag 508, consistent with one or more exemplary embodiments of the present disclosure. Referring to FIG. 5A, reference numeral 500 refers to a resuscitation management device including all illustrated elements except for the resuscitation bag, which is referred to by reference numeral 508. In an exemplary embodiment, resuscitation management device 500 may include a sensor assembly 501 similar to sensor assembly 202 that may be mounted on an outer surface of resuscitation bag 508 similar to resuscitation bag 308.

In an exemplary embodiment, sensor assembly 501 may include an accelerometer that may be mounted on the outer surface of resuscitation bag 508 such that an axis along which resuscitation bag 508 may be compressed may pass through sensor assembly 501. For example, resuscitation bag 508 may be compressed along an axis 504 and sensor assembly 501 may be mounted such that axis 504 may pass through sensor assembly 501. In an exemplary embodiment, sensor assembly 501 may be configured to measure an acceleration/deceleration of a point on the outer surface of resuscitation bag 508 on which sensor assembly 501 is mounted. In an exemplary embodiment, sensor assembly 501 may further be configured to detect a spatial direction along which acceleration/deceleration occurs. For example, when resuscitation bag 508 is compressed along axis 504 in a direction shown by arrow 503, sensor assembly 501 may detect an acceleration/deceleration along the direction shown by arrow 503 and furthermore detects a spatial direction of acceleration/deceleration to be along axis 504. In an exemplary embodiment, such acceleration/deceleration detected by sensor assembly 501 is due to the motion of sensor assembly 501 from a decompressed state of resuscitation bag 508 to an adequately compressed state of resuscitation bag 508'. Here, sensor assembly 501 is designated by reference numeral 501' on the adequately compressed resuscitation bag 508'.

For example, when a user compresses resuscitation bag 508, the outer surface of resuscitation bag 508 accelerates inwardly along a direction shown by arrow 503 and as resuscitation bag 508 approaches an adequately compressed state 508', the outer surface of resuscitation bag 508 decelerates until the outer surface comes to a complete stop at the end of one compression of resuscitation bag 508. Consequently, when a user compresses resuscitation bag 508, sensor assembly 501 accelerates inwardly along the direction shown by arrow 503 and as resuscitation bag 508 approaches an adequately compressed state 508', sensor assembly 501 decelerates until sensor assembly 501 comes to a complete stop at the end of one compression of resuscitation bag 508. In an exemplary embodiment, sensor assembly 501 on adequately compressed resuscitation bag 508' is designated by reference numeral 501'. After compression of resuscitation bag 508, compressed resuscitation bag 508' may be released by a user and resuscitation bag 508 returns to its initial decompressed state and a motion path opposite the one described above is taken, where sensor assembly 501 may first accelerate back along a direction opposite the direction shown by arrow 503 and then sensor assembly 501 may decelerate to its initial position.

In an exemplary embodiment, as discussed in the preceding paragraph, during a single compression/decompression of resuscitation bag 508, sensor assembly 501 mounted on the outer surface of resuscitation bag 508 may assume a motion with variable acceleration and may measure all the changes in acceleration during a single compression/decompression of resuscitation bag 508. In other words, sensor assembly 501 may be configured to measure acceleration as a function of time during a single compression/decompression of resuscitation bag 508. In an exemplary embodiment, the velocity or speed of compression as a function of time may be obtained by integrating the measured acceleration/deceleration as the function of time over the duration of a single compression/decompression of resuscitation bag 508. Similarly, an extent of compression as a function of time may be obtained by integrating the measured velocity as a function of time over the duration of a single compression/decompression of resuscitation bag 508. In other words, a calibration correlation or a lookup table may be obtained that may correlate the measured acceleration/deceleration with an extent of compression of resuscitation bag 508 at any given moment during a single compression/decompression of resuscitation bag 508.

In an exemplary embodiment, sensor assembly 202 may be similar to sensor assembly 501 and may include an accelerometer. In an exemplary embodiment, memory 212 may further store the calibration curve or the look up table that may provide a correlation between an extent and speed of compression of resuscitation bag 508 with the measured acceleration/deceleration during a certain time interval. In an exemplary embodiment, memory 212 may further store executable instructions to urge processor 210 to receive an output signal from sensor assembly 202 that may include information on an amount of acceleration/deceleration and a spatial direction of acceleration/deceleration measured by sensor assembly 202 and utilize the stored calibration curve or the lookup table to determine an extent and speed of compression of resuscitation bag 508.

In an exemplary embodiment, such utilization of an accelerometer as sensor assembly 501 may be used when resuscitation bag 508 does not have any other translational movements. An exemplary scenario where an exemplary resuscitation bag does not have any additional translational movements is when a non-moving patient is laid down on the floor of a room and a user is utilizing an exemplary resuscitation bag to resuscitate the patient. However, in an exemplary embodiment, an exemplary accelerometer may also be used in scenarios where an exemplary resuscitation bag has additional translational movements, for example, when a user may be resuscitating a patient in a moving ambulance. Such additional movements may lead to an exemplary accelerometer utilized as sensor assembly 501 to measure additional acceleration/deceleration elements corresponding to such additional movements. In other words, an output signal of sensor assembly 501 may represent information on compression/decompression of resuscitation bag 508 and movements of resuscitation bag 508 due to the movements of the environment, in which resuscitation process is being carried out. Such additional information on movements of resuscitation bag 508 must be accounted for and possibly be eliminated so that resuscitation management system 200 may utilize the output signals of sensor assembly 202 for calculating breathing parameters.

Figure 5B:
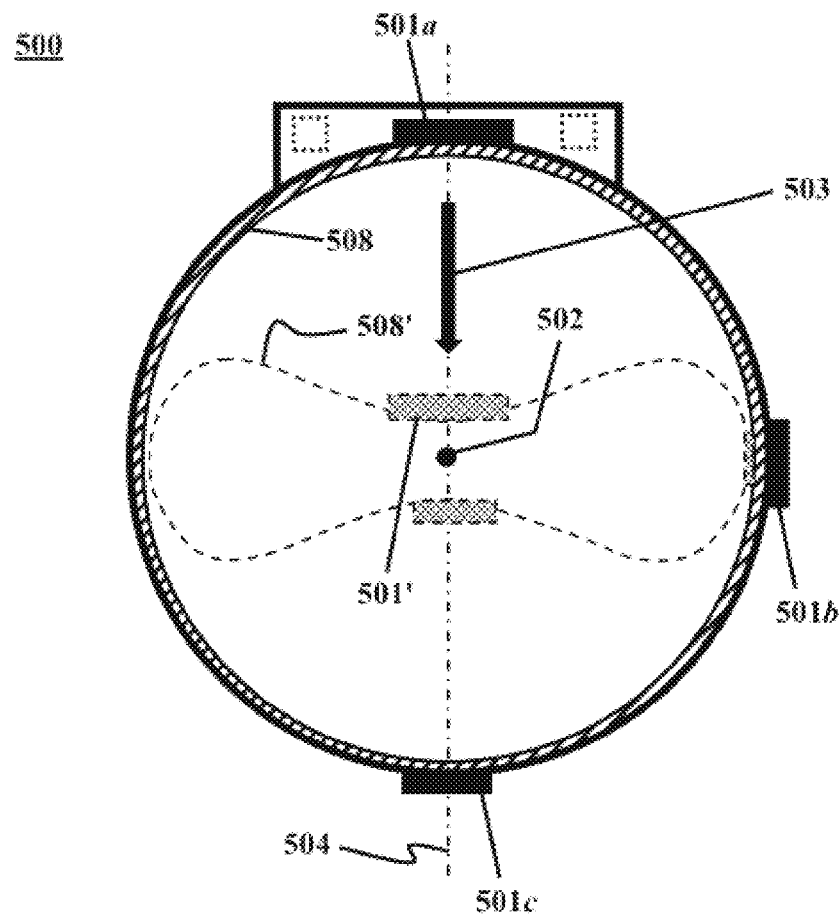
FIG. 5B illustrates a schematic front view of a resuscitation management device mounted around a resuscitation bag, consistent with one or more exemplary embodiments of the present disclosure.

FIG. 5B illustrates a schematic front view of a resuscitation management device 500 mounted around a resuscitation bag 508, consistent with one or more exemplary embodiments of the present disclosure. In an exemplary embodiment, in an exemplary scenario when resuscitation bag 508 is moving in an exemplary moving vehicle, sensor assembly 501 may include a first accelerometer 501a and at least one additional accelerometer such as accelerometers (501b and 501c) that may either be mounted on an opposite side of resuscitation bag 508 along axis 504, such as accelerometer 501c or may be mounted on the outer surface of resuscitation bag near first accelerometer 501a, such as accelerometer 510b. In an exemplary embodiment, first accelerometer 501a may measure a first acceleration vector and an additional accelerometer such as accelerometer 501c may measure a second acceleration vector for each compression/ decompression of resuscitation bag 508. In an exemplary embodiment, first acceleration vector is the sum of two acceleration vectors, an acceleration vector of compression/decompression motion of resuscitation bag 508 and an acceleration vector of translational movement of resuscitation bag. Similarly, second acceleration vector is the sum of two acceleration vectors, an acceleration vector of compression/decompression motion of resuscitation bag 508 and an acceleration vector of translational movement of resuscitation bag 508. In an exemplary embodiment, the acceleration vectors of translational movement of resuscitation bag 508 measured by first accelerometer 501a and accelerometer 501c may be the same, since both first accelerometer 501a and accelerometer 501c are moving with the vehicle in the same direction with the same acceleration. Consequently, by subtracting the second acceleration vector form the first acceleration vector, a resultant vector may be obtained that may include information on a magnitude of acceleration/deceleration and a spatial direction of acceleration/deceleration of compression/decompression motion of resuscitation bag 308.

In an exemplary embodiment, memory 212 may further include executable instructions that may urge processor 210 to receive the output signal or the plurality of output signals from first accelerometer 501a as a first acceleration vector, receive the output signal or the plurality of output signals from at least one of accelerometers (501b and 501c) as a second acceleration vector, and obtain a resultant acceleration vector by subtracting the second acceleration vector from the first acceleration vector. In an exemplary embodiment, memory 212 may further include executable instructions that may urge processor 210 to calculate an extent and speed of compression/decompression of resuscitation bag 508 based on the obtained resultant acceleration vector and the calibration curve or the lookup table correlating an acceleration vector measured for resuscitation bag 508 with an extent and speed of compression/decompression of resuscitation bag 508.

In an exemplary embodiment, sensor assembly 501 may include an accelerometer, such as one or a combination of various types of accelerometers, such as a triple axis accelerometer, a microelectromechanical accelerometer, a bulk micromachined capacitive accelerometer, a bulk micromachined piezoelectric resistive accelerometer, a capacitive spring mass system base accelerometer, a DC-response accelerometer, an electromechanical servo (Servo Force Balance) accelerometer, a high gravity accelerometer, a high temperature accelerometer, a Laser accelerometer, a low frequency accelerometer, a magnetic induction accelerometer, a modally tuned impact hammers accelerometer, a null-balance accelerometer, an optical accelerometer, a Pendulous integrating gyroscopic accelerometer (PIGA), a piezoelectric accelerometer, a quantum (rubidium atom cloud, laser cooled) accelerometer, a resonance accelerometer, a seat pad accelerometer, a shear mode accelerometer, a strain gauge accelerometer, a surface acoustic wave (SAW) accelerometer, a surface micromachined capacitive (MEMS) accelerometer, a thermal (submicrometric CMOS process) accelerometer, a triaxial accelerometer, a vacuum diode with flexible anode accelerometer, a potentiometric type accelerometer, and a LVDT type accelerometer.

Figure 6A:
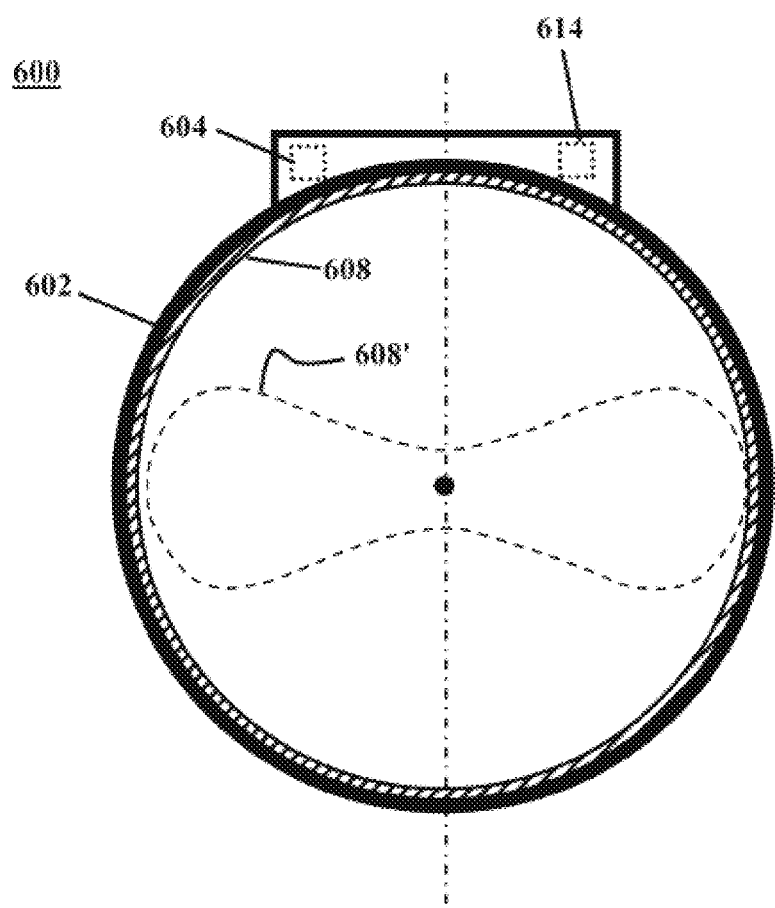
FIGS. 6A and 6B illustrate schematic front views of a resuscitation management device mounted around a resuscitation bag, consistent with one or more exemplary embodiments of the present disclosure.
Figure 6B:
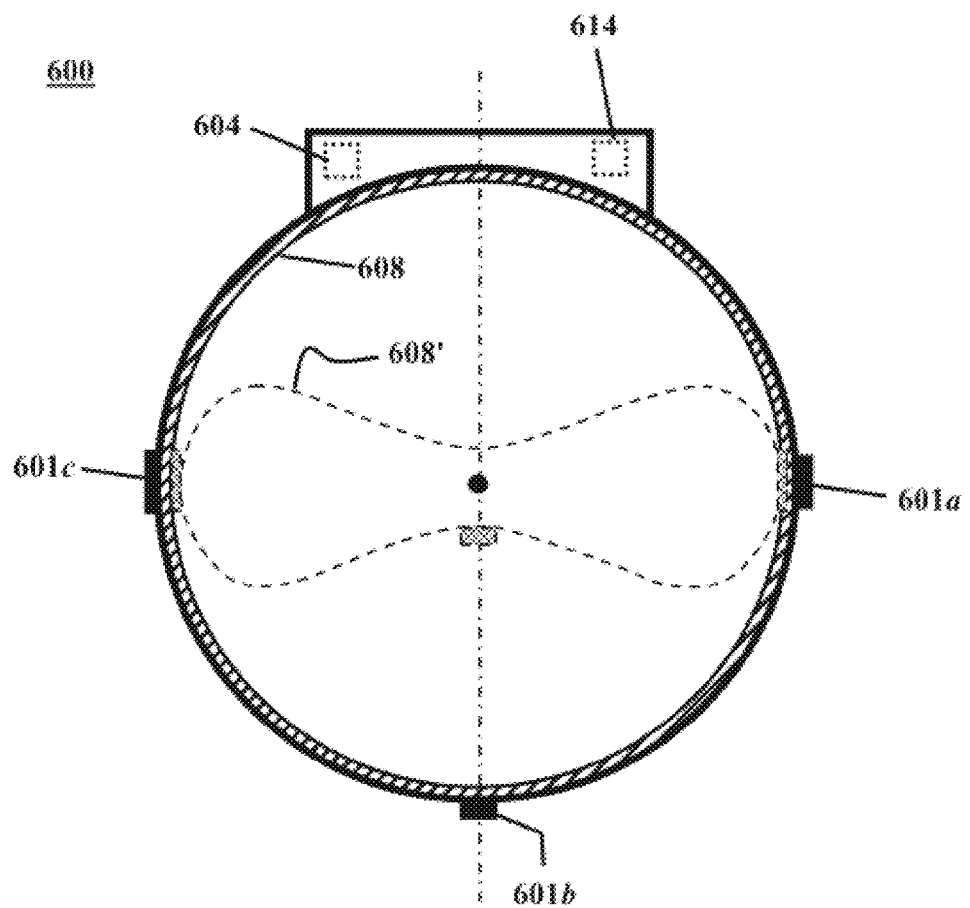

FIGS. 6A and 6B illustrate schematic front views of a resuscitation management device 600 mounted around a resuscitation bag 608, consistent with one or more exemplary embodiments of the present disclosure. In an exemplary embodiment, resuscitation management device 600 may be similar to resuscitation management system 200 and resuscitation bag 608 may be similar to resuscitation bag 108. In an exemplary embodiment, resuscitation management device 600 may include a sensor assembly 602 similar to sensor assembly 202 that may be coupled with a processing unit 604 similar to processing unit 204 and an I/O interface 614 similar to I/O interface 214.

In an exemplary embodiment, sensor assembly 602 may include a pressure/tension sensor that may be attached to an outer surface of resuscitation bag 608. In an exemplary embodiment, pressure/tension sensor as sensor assembly 602 may be configured to sense a state of resuscitation bag 608 between a decompressed state (designated by 608) and a compressed state (designated by 608') based at least in part on an amount of pressure exerted by a user's hand on resuscitation bag 608 during compression of resuscitation bag 608. In an exemplary embodiment, sensor assembly 602 may be mounted on resuscitation bag 608 such that a user may press on sensor assembly 602 to compress resuscitation bag 608. In an exemplary embodiment, sensor assembly 602 may be configured to generate an output signal indicative of at least the amount of pressure sensed.

In an exemplary embodiment, memory 212 may further store calibration data to associate the amount of pressure within the time interval of exerting the amount of pressure, with an extent of compression of an exemplary resuscitation bag and executable instructions that may urge processor 210 to receive an output signal of sensor assembly 602 at a given moment and then may utilize the stored calibration data to calculate the extent of compression of resuscitation bag 608 at the given moment.

In an exemplary embodiment, sensor assembly 602 may be a pressure/tension sensor unit that may be wrapped around resuscitation bag 608 as illustrated schematically in FIG. 6A. In an exemplary embodiment, sensor assembly 602 may include at least one of a force-sensitive resistor or a pressure-sensitive conductive sheet, which may be wrapped around resuscitation bag 608.

In an exemplary embodiment, sensor assembly 602 may include a plurality of pressure/tension sensors that may be attached on different parts of an outer surface of resuscitation bag 608. For example, sensor assembly 602 may include pressure/tension sensors (601a-601c). In an exemplary embodiment, pressure/tension sensors (601a-601c) may include at least one of force-sensitive resistor pressure sensor, a linear soft potentiometer pressure sensor, a load cell, a capacitive trackpad, a capacitive touchpad, a piezoresistive strain gauge including a polysilicon thin film, bonded metal foil, thick film, silicon-on-sapphire, and sputtered thin film, a capacitive pressure sensor, an electromagnetic pressure sensors, a piezoelectric pressure sensor, an optical pressure sensor, and a potentiometric pressure sensor.

Figure 7:
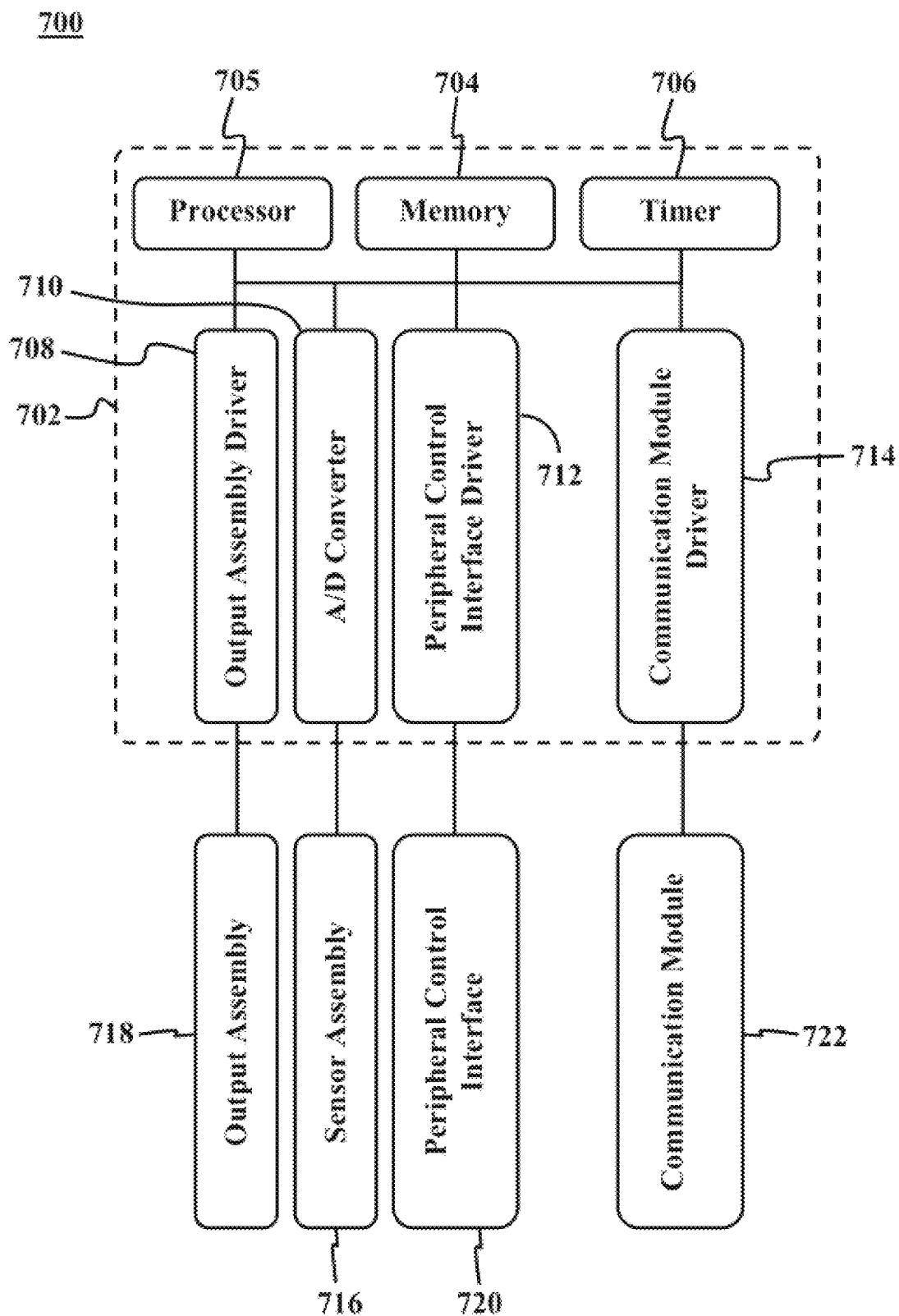
FIG. 7 illustrates a functional block diagram of a resuscitation management system, consistent with one or more exemplary embodiments of the present disclosure.

FIG. 7 illustrates a functional block diagram of a resuscitation management system 700, consistent with one or more exemplary embodiments of the present disclosure. In an exemplary embodiment, resuscitation management system 700 may be functionally similar to resuscitation management system 200. In an exemplary embodiment, resuscitation management system 200 and resuscitation management system 700 may be functionally and/or structurally similar to resuscitation management device 100.

In an exemplary embodiment, resuscitation management system 700 may include a processing unit 702 similar to processing unit 204. In an exemplary embodiment, processing unit 702 may include at least one memory 704 similar to memory 212, and at least one processor 705 similar to processor 210 that may be coupled with memory 704. In an exemplary embodiment, processing unit 702 may further include a timer 706, an output assembly driver 708, an analog to digital (A/D) converter 710, a peripheral control interface driver 712, and a communication module driver 714. In an exemplary embodiment, resuscitation management system 700 may further include a sensor assembly 716 that may be similar to sensor assembly 202 and may be coupled to processing unit 702 via A/D converter 710. In an exemplary embodiment, resuscitation management system 700 may further include an output assembly 718 that may be coupled to output assembly driver 708, a peripheral control interface 720 that may be coupled to peripheral control interface driver 712, a communication module 722 that may be coupled to communication module driver 714. In an exemplary embodiment, elements of resuscitation management system 700 may be coupled with each other via a wired, wireless, or a combination of wired and wireless network, which is represented by connecting solid lines in FIG. 7. For simplicity, some routine elements such as power supplies, touch screen interfaces, buttons, switches, electronic jumpers, and wires and/or connectors are omitted. In an exemplary embodiment, various elements of processing unit 702 may be directly connected to other elements of resuscitation management system 700 or may be indirectly connected to other elements via an internal network of wired, wireless, or a combination of wired and wireless network, illustrated by solid interconnecting lines in FIG. 7. In an exemplary embodiment, various elements of processing unit 702 may be indirectly connected to other elements of resuscitation management system 700 via communication module driver 714 or an external network (not illustrated).

In an exemplary embodiment, memory 704 may be a computer-readable media or a volatile memory unit or a non-volatile memory unit. In an exemplary embodiment, memory 704 may be a hard disk, a floppy disk, a tape device, a flash memory data storage device, a thumb drive, a solid-state memory (SSD), a read-only memory (ROM), or an optical disk device, or any other similar memory devices or storage devices.

In an exemplary embodiment, memory 704 may be configured to store software, codes, or other forms of executable instructions that may be retrieved by processor 705 or other components of processing unit 702 to enable them to perform various functions. In an exemplary embodiment, each of the various components of processing unit 702, such as processor 705 may include internal storages to store their software instructions or codes to enable them to perform various functions without requiring memory 704.

In an exemplary embodiment, memory 704 may further contain reference tables including the limits of target values that may be used to compare or interpret the measurements received from sensor assembly 716. For example, memory 704 may include a target number of breaths per certain time intervals according to the determined type of patient, target range of certain breathing parameters, such as I:E ratio, tidal volume, or minute ventilation according to the determined type of a patient and medical condition of a patient. As used herein, determining a type for a patient may refer to determining if a patient is adult, child or infant and if a patient is a human or animal.

In an exemplary embodiment, memory 704 may further contain information and/or executable instruction to control the operation of the various components of processing unit 702, for example running various components of resuscitation management system 700, testing various components of resuscitation management system 700, such as testing the battery capacity, or calibrating various components of resuscitation management system 700.

In an exemplary embodiment, processing unit 702 may store all or part of the measured values throughout a resuscitation event performed by a manual resuscitation bag similar to manual resuscitator 102. In an exemplary embodiment, the stored values may include one or a combination of multiple parameters, such as the age of the patient (infant, child, adult), the type of the patient (human, animal), the time and date of the resuscitation event, the total number of breaths delivered to the patient, the total number of proper breaths delivered to the patient, the total number of improper breaths delivered to the patient, breathing rate at each time point; average breathing rate per certain time interval, retrieved values from a reference table that may be stored in memory 704, squeezing or compressing speed of bag 104 of manual resuscitator 102, duration of inspirations, duration of expirations, time interval between any inspiration and expiration, or any other similar measured parameters by sensor assembly 716 or calculated parameters by processor 705.

In an exemplary embodiment, processing unit 702 may transfer the stored parameters on memory 704 to an external system, such as a computer, a tablet, or a mobile phone via communication module driver 714, or directly via communication module 722. Such stored history of measured and calculated data may be used for further evaluation of the quality of a given resuscitation event, or performance of a user during a resuscitation event. In certain cases, where a resuscitated patient may not survive, the history may provide evidence of an acceptable performance of artificial breathing, which may later be used to rule out hyperventilation or hypoventilation as a cause of death.

In an exemplary embodiment, peripheral control interface driver 712 may be connected to peripheral control interface 720 of resuscitation management system 700. In an exemplary embodiment, peripheral control interface 720 may be configured similar to I/O interface 214 of resuscitation management system 200 and may include touchscreens, buttons, switches, keypads, or potentiometers to let a user, such as a caregiver interact with processing unit 702 to initiate, continue or stop desired functions, or to input, alter, or delete at least one of the target values, the calculated values, or the calculated derivative values. In an exemplary embodiment, peripheral control interface 720 may be used to turn on or off resuscitation management system 700.

Figure 8:
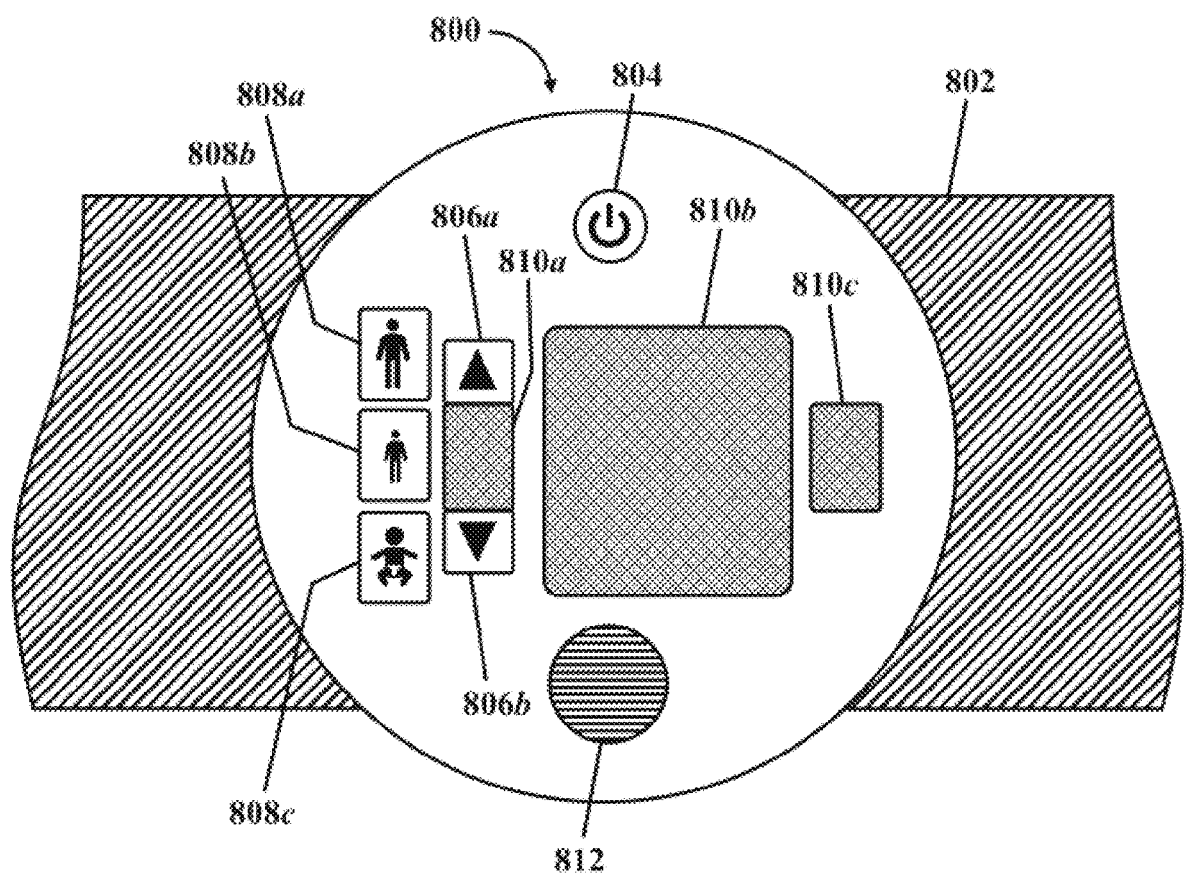
FIG. 8 illustrates a resuscitation management device, consistent with one or more exemplary embodiments of the present disclosure.

FIG. 8 illustrates a resuscitation management device 800, consistent with one or more exemplary embodiments of the present disclosure. In an exemplary embodiment, resuscitation management device 800 may be similar to resuscitation management device 100. In an exemplary embodiment, resuscitation management device 800 may be attached to a manual resuscitator, such as manual resuscitator 102 by utilizing a flexible band, such as flexible band 802. In an exemplary embodiment, I/O interface 214 of resuscitation management system 200 may be configured as peripheral control interface 720 and output assembly 718 of system 700. In an exemplary embodiment, resuscitation management device 800 may include a peripheral control interface similar to peripheral control interface 720, which is referred to herein after with the same reference numeral. In an exemplary embodiment, peripheral control interface 720 may include an On/Off switch 804 that may be utilized for turning resuscitation management device 800 on or off In an exemplary embodiment, peripheral control interface 720 may further include adjustment buttons (806a and 806b) that may be utilized for adjusting various parameters, such as a desired breathing rate, a brand name of an exemplary manual resuscitator being used, and a type of compression (on-handed or two-handed). In an exemplary embodiment, peripheral control interface 720 may further include optional buttons (808a, 808b, and 808c) that may be utilized by a user to select an age group for a patient. For example, button 808a may be dedicated to selecting an adult age group, button 808b may be dedicated to selecting a child age group, and button 808c may be dedicated to selecting an infant age group.

In an exemplary embodiment, memory 212 may further store a database of commercially available manual resuscitators and their associated parameters, such as their respective volumes. In an exemplary embodiment, adjustment buttons (806a and 806b) may further be utilized to select a specific manual resuscitator from the stored database of commercially available manual resuscitators. In an exemplary embodiment, memory 212 may further store volumetric data for one-handed and two-handed compression of each respective commercially available manual resuscitators. Each commercially available manual resuscitator may have a specific internal volume and compressing an exemplary bag of a manual resuscitator by one hand or two hands may push out different volumes of breathing gases out of an exemplary bag. In an exemplary embodiment, such volumetric data for commercially available manual resuscitators and volumetric data for one-handed and two-handed compression of each respective commercially available manual resuscitator may allow for calculating various volumes of breathing gases delivered to a patient in various scenarios created due to utilizing different manual resuscitators and different types of compression (one-handed or two handed).

In an exemplary embodiment, memory 212 may further store executable instructions to urge processor 210 to calculate an extent of compression of an exemplary resuscitation bag 508 based at least in part on the amount of displacement of the sensing element 501 mounted on exemplary resuscitation bag 508 between a decompressed state and a compressed state. In other words, for a given change in a distance between sensing element 501 at decompressed state of exemplary resuscitation bag 508, and sensing element 501' at a compressed state of exemplary resuscitation bag 508, processor 705 may be configured to calculate how much an internal volume of bag 508 may change, based at least in part on volumetric data stored in memory 704 for each commercially available manual resuscitator.

In another exemplary embodiment, where there are more than one exemplary sensing elements such as sensing elements (501a and 501c or 601a and 601c), memory 212 may further store executable instructions to urge processor 210 to calculate an extent of compression of an exemplary resuscitation bag 508 based at least in part on the amount of relative displacement of the exemplary sensing elements (501a & 501c or 601a & 601c) mounted on exemplary resuscitation bag 508 between a decompressed state and a compressed state.

In an exemplary embodiment, memory 212 may further store a 'bag compression-breathing volume' curve that may provide information regarding a volume of a delivered ventilation based at least in part on an extent of compression of bag 104. As used herein, a bag compression-breathing volume curve may be obtained for each available manual resuscitator by calibration measurements. An exemplary bag compression-breathing volume may correlate an extent of compression of a bag to a volume of breathing gases pushed out of the bag for that extent of compression. For example, an exemplary compression-breathing volume may show how much breathing gas will be pushed out of a specific commercially available bag for a 50% compression of that specific commercially available bag. In an exemplary embodiment, memory 212 may further store two 'bag compression-breathing volume' curves for each commercially available manual resuscitator, one curve for a one-handed compression of a bag of the manual resuscitator and one curve for a two-handed compression of the bag of the manual resuscitator. For example, a bag compression-breathing volume curve for a one-handed compression of a commercially available adult Ambu Spur II manual resuscitator may show that a 50% one-handed compression of a bag of the adult Ambu Spur II manual resuscitator with a 1475 ml volume may deliver 500 ml of air into a patient's airways. In another example, a bag compression-breathing volume curve for a two-handed compression of a commercially available adult Ambu Spur II manual resuscitator may show that a 50% two-handed compression of a bag of the adult Ambu Spur II manual resuscitator with a 1475 ml volume may deliver 1100 ml of air into a patient's airways.

In an exemplary embodiment, memory 212 may further store executable instructions to urge processor 210 to calculate a tidal volume based at least in part on the stored 'bag compression-breathing volume' curves. In an exemplary embodiment, memory 212 may further store executable instructions to urge processor 210 to calculate a minute ventilation based at least in part on the calculated tidal volume and the calculated breathing rate.

In an exemplary embodiment, output assembly 718 may include one or a combination of multiple displays (810a, 810b, and 810c), at least one audio device 812, at least one tactile device, such as a vibrator (not illustrated), and at least one mechanical actuator. In an exemplary embodiment, multiple displays (810a, 810b, and 810c) may refer to two-dimensional monochrome displays, color displays, touch screens, liquid crystal displays, electronic paper, electrophoretic displays, electroluminescent displays, seven-segment displays, organic light-emitting diode (OLED or organic LED), or any other relevant visual device. In an exemplary embodiment, display 810a may display an optimal value for the breathing per minute based at least in part on the age group, patient type, or a desirable breathing rate selected by a user.

In an exemplary embodiment, memory 212 may store executable instructions to urge processor 210 to calculate time-intervals between compressions of bag 104 based at least in part on the target breathing parameters, such as the target breathing rate. For example, for a target breathing rate of 12 breaths per minute, processor 210 may calculate the time interval between each pair of consecutive compressions to be 5 seconds. In an exemplary embodiment, memory 212 may store executable instructions to urge processor 210 to readjust time-intervals between compressions of bag 104 based on the performance of a user. For example, for a target breathing rate of 12 breaths per minute, responsive to a user having delivered only 5 breaths in 30 seconds instead of 6 breathes, processor 210 may be configured to readjust the time interval between the remaining 7 breaths to achieve the target breathing rate of 12 breaths per minute. For example, the time interval between the remaining breaths for the next 150 seconds may be readjusted to 4.83 seconds to gradually achieve the target breathing rate of 12 breaths per minute. In an exemplary embodiment, memory 212 may further store executable instructions to urge output assembly 718 to provide alarms corresponding to readjusted time intervals to guide a user to achieve target breathing parameters.

Figure 9:
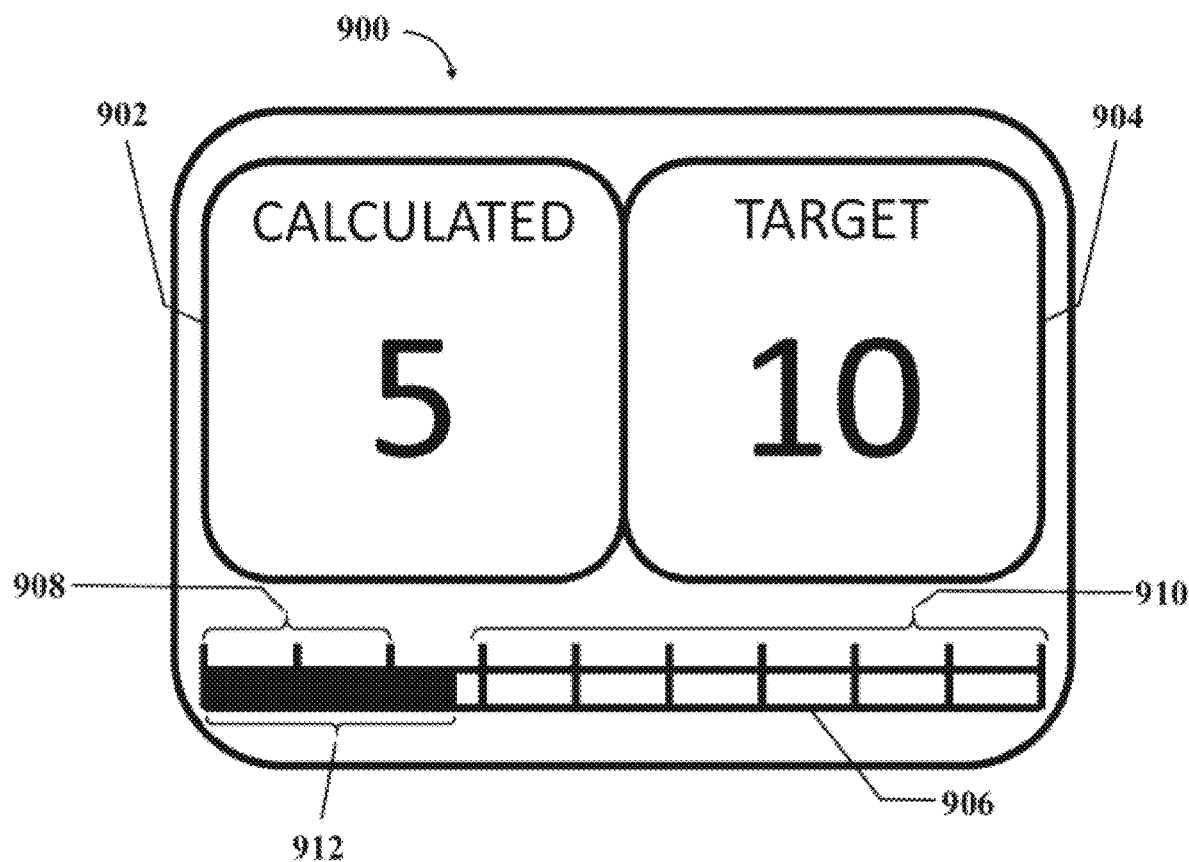
FIG. 9 illustrates a display of an output assembly, consistent with one or more exemplary embodiments of the present disclosure.

FIG. 9 illustrates a display 900 of output assembly 718, consistent with one or more exemplary embodiments of the present disclosure. In an exemplary embodiment, display 900 may be similar to display 810b. In an exemplary embodiment, display 900 may display various information regarding the operation and functions of a manual resuscitator coupled with a resuscitation management device similar to resuscitation management device 800 and various information regarding the resuscitation procedure. In an exemplary embodiment, display 900 may further display one or a combination of multiple values, such as a calculated breathing rate 902, a target breathing rate 904, alarm notifications (not illustrated), a timeline 906 illustrating timepoints 908 of given breaths and timepoints 910 of upcoming breaths based at least in part on one of the calculated breathing rate and calculated time intervals between consecutive compressions. In an exemplary embodiment, display 900 may further display a progress bar 912 illustrating time elapsed since the start of a certain breathing period. For example, timeline 906 may represent a 60 seconds breathing period, and progress bar 912 may illustrate that 14 seconds has passed since the start of a 60 seconds breathing period.

In an exemplary embodiment, display 900 may further display one or a combination of multiple values, such as an indication to show if the user is hypo-ventilating, normo-ventilating, or hyperventilating the patient, an indication to show the compression, or decompression of bag 104, an indication to show if the squeezing of bag 104 has been adequate to deliver a proper breathing; duration of compression or decompression of bag 104, compression/decompression speed, compression rate per minute or any arbitrary time interval, occurrence or non-occurrence of inspiration or expiration, calculated I:E ratio, target I:E ratio, elapsed time from the beginning of a resuscitation event, calculated tidal volume, target tidal volume, calculated minute ventilation, and target minute ventilation.

In an exemplary embodiment, display 900 may display a value, such as an exemplary value of current breathing rate per minute that is being delivered to a patient, and may be an average of the number of the delivered breaths per certain time interval.

In an exemplary embodiment, output assembly 718 may further include one or more of monochrome light-emitting diodes (LEDs), multicolor LEDs, incandescent bulbs, surface mounted device (SMD) electroluminescent diode, or any other light-emitting elements. In an exemplary embodiment, audio device 712 may include a speaker, buzzer, piezo, or tone generator. In an exemplary embodiment, the tactile device may include one or a combination of pneumatic vibrators, electric vibrators, and hydraulic vibrators. In an exemplary embodiment, the vibrator may be an electric motor with an unbalanced mass on its driveshaft.

In an exemplary embodiment, output assembly 718 may provide alarms including one or a combination of multiple visual indications, such as light-emitting elements that are selectively turned on or turned off; audio indications that are generated by a speaker, buzzer, piezo, or tone generator; tactile indications that are generated by a vibrator; and mechanical indications that are generated by a mechanical actuator. In an exemplary embodiment, the alarm may be a lack of one or a combination of multiple visual indications, audio indications, tactile indications, or mechanical indications. For example, a visual, audio, or tactile signal may be generated continuously when there is no alarm, such as playing an audio signal of a certain frequency or a combination of various frequencies, when the user is using the bag-valve-mask in a target range of breathing parameters, such as delivering the target rate of breathing. In an exemplary embodiment, the alarm may be presented as a change in one or a combination of multiple visual indications, audio indications, or tactile indications. For example, a visual, audio, or tactile signal may change when there is an alarm, such as playing an audio signal of a different frequency, or a combination of various frequencies, when the user is not using the bag-valve-mask in a target range of breathing parameters (such as delivering a non-target rate of breathing).

Figure 10:
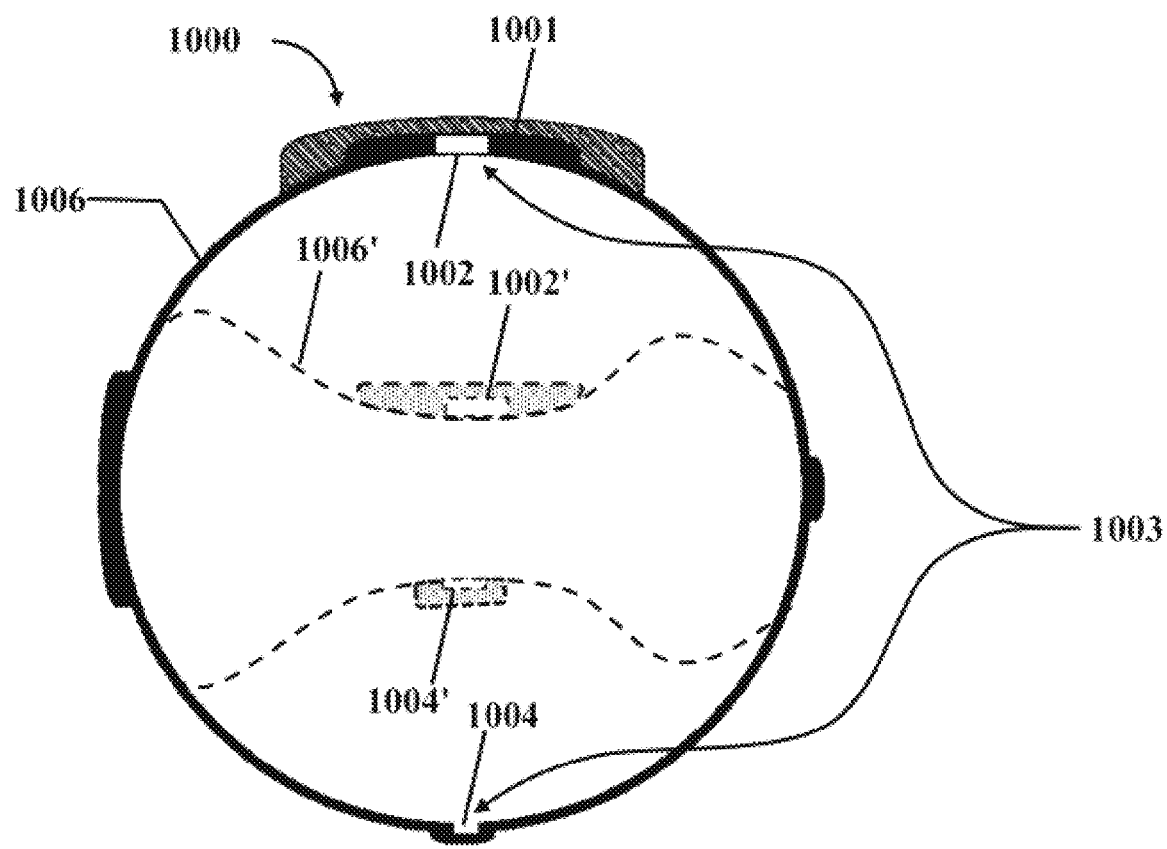
FIG. 10 illustrates a resuscitation management device, consistent with one or more exemplary embodiments of the present disclosure.

FIG. 10 illustrates a resuscitation management device 1000, consistent with one or more exemplary embodiments of the present disclosure. In an exemplary embodiment, resuscitation management device 1000 may be similar to resuscitation management device 100. In an exemplary embodiment, resuscitation management device 1000 may include a sensor assembly 1001 similar to sensor assembly 101. In an exemplary embodiment, resuscitation management device 1000 may further include a mechanical actuator 1003 that may be configured to generate mechanical indications. In an exemplary embodiment, mechanical actuator 1003 may include an attracting element 1002 and an attractable element 1004. In an exemplary embodiment, attracting element 1002 and attractable element 1004 may include elements that may be arbitrarily magnetized to generate an electromagnetic field with a certain polarity and strength. For example, attracting element 1002 and attractable element 1004 may include a pair of electromagnets mounted on opposite sides of a resuscitation bag 1006 along an axis perpendicular to a longitudinal axis of resuscitation bag 1006. In an exemplary embodiment, such utilization of electromagnets as attracting element 1002 and attractable element 1004 may allow for selectively magnetizing attracting element 1002 and attractable element 1004 to either attract each other or repulse each other. Such attraction and repulsion of attracting element 1002 and attractable element 1004 may force resuscitation bag 1006 to be compressed or decompressed on demand. For example, attracting element 1002 and attractable element 1004 may be magnetized such that opposite poles of attracting element 1002 and attractable element 1004 may face each other, which may lead to attracting element 1002 and attractable element 1004 attracting each other from a decompressed state to a compressed state designated by dash lines. Attracting element in the compressed state is referred to by reference numeral 1002' and attractable element in the compressed state is referred to by reference numeral 1004'. In an exemplary embodiment, mechanical actuator 1003 may be a part of an output assembly similar to output assembly 718. In an exemplary embodiment, attracting element 1002 and attractable element 1004 may be coupled with a processing unit (not illustrated) similar to processing unit 702 either directly or via an output assembly driver (not illustrated) similar to output assembly driver 708.

In an exemplary embodiment, processing unit 702 may be configured to urge attracting element 1002 and attractable element 1004 to attract or repulse each other by sending command signals in the form of electric currents to attracting element 1002 and attractable element 1004. In an exemplary embodiment, processing unit 702 may be configured to manipulate polarities and strengths of magnetic fields generated by attracting element 1002 and attractable element 1004 by manipulating directions and amounts of the electric currents applied to attracting element 1002 and attractable element 1004. In an exemplary embodiment, attractable element 1004 may further include a magnetic element, such as a permanent magnet or a ferromagnetic material.

As mentioned before, in an exemplary embodiment, output assembly 718 may provide alarms by generating mechanical indications. In an exemplary embodiment, such mechanical indications may be generated by mechanical actuator 1003. For example, when a user is hyperventilating a patient, processing unit 702 may urge attracting element 1002 or attractable element 1004 to generate a magnetic field with a certain polarity and strength, such that attracting element 1002 and attractable element 1004 may attract each other to retain resuscitation bag 1006 in a compressed state (designated by dash lines and referred to by 1006'). In an exemplary embodiment, attracting element 1002 and attractable element 1004 attracting each other and thereby forcing resuscitation bag 1006 to remain in a compressed state in response to a user hyperventilating a patient, may allow for locking resuscitation bag 1006 and mechanically preventing the user to continue hyperventilation.

In an exemplary embodiment, peripheral control interface 720 may further be used to adjust other parameters and functions relevant to the operation of resuscitation management device 800, such as adjusting the target breathing rate, I:E ratio, or tidal volume, or minute ventilation, calibrating the sensor assembly, or muting output assembly 718. In an exemplary embodiment, the adjustments via peripheral control interface 720 may retrieve certain values from a reference table that may be stored in a memory of resuscitation management device 600, which may be configured similar to memory 704.

In an exemplary embodiment, processing unit 702 may further be configured to receive output signals of sensor assembly 716 and based at least in part on the received signals, initiate certain functions, such as turning on and off certain elements of resuscitation management system 700. For example, processing unit 702 may be configured to detect inactivity of the resuscitator, based at least in part on the received output signals of sensor assembly 716 and may initiate certain functions of resuscitation management system 700, such as presenting an alarm or turning off resuscitation management system 700, or even putting certain elements of resuscitation management system 700 to a low-power mode.

In an exemplary embodiment, utilizing such resuscitation management systems and devices similar to resuscitation management devices (100 and 800) or resuscitation management systems (200 and 700) may allow for determining if a manual resuscitator, such as manual resuscitator 102 is compressed or not, the duration of the compression, or the duration of lack of compression of bag 104; the speed of compression, or the speed of decompression of bag 104, number of compressions of bag 104, number of decompression of bag 104, rate of breathing per minute, rate of breathing during any arbitrary time intervals; or occurrence or non-occurrence of an inspiration or an expiration during a certain time interval.

In an exemplary embodiment, processing unit 702 may further be configured to store all or part of the measured values throughout a resuscitation event in memory 704. As used herein, the measured values throughout a resuscitation event may be one or a combination of multiple parameters, such as the age group of a patient, type of a patient, time and date of the resuscitation event, total number of breaths delivered to the patient, total number of proper breathing delivered to the patient, total number of improper breathing delivered to the patient, breathing rate at each time point, the average breathing rate per certain time interval, the speed of the squeezing of a resuscitating bag, such as bag 104, duration of any inspirations, duration of any expirations, time interval between any inspiration and expiration, and other similar parameters.

In an exemplary embodiment, processing unit 702 may further be configured to transfer the aforementioned stored parameters to an external system, such as a computer, a tablet, or a mobile phone via the communication module driver 714, or directly via communication module 722. In an exemplary embodiment, such stored parameters may be used for further evaluation of the quality of a resuscitation event, or the performance of a caregiver during a resuscitation event. For example, in case a patient dies during a resuscitation event, the stored parameters may provide evidence that may be utilized in an investigation for cause of death.

In an exemplary embodiment, processing unit 702 may further be configured to receive new executable instructions, for reconfiguring the built-in operating system (BIOS), or the firmware, or the software of the components of resuscitation management system 700. Such new executable instructions may temporarily or permanently be stored on memory 704.

The embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for description and not of limitation, such that the terminology or phraseology of the present specification is to be interpreted by the skilled artisan in light of the teachings and guidance.

The breadth and scope of the present disclosure should not be limited by any of the above-described exemplary embodiments but should be defined only in accordance with the following claims and their equivalents.

Throughout this specification and the claims which follow, unless the context requires otherwise, the word "comprise", and variations such as "comprises" or "comprising", will be understood to imply the inclusion of a stated integer or step or group of integers or steps but not to the exclusion of any other integer or step or group of integers or steps. Moreover, the word "substantially" when used with an adjective or adverb is intended to enhance the scope of the particular characteristic, e.g., substantially planar is intended to mean planar, nearly planar and/or exhibiting characteristics associated with a planar element. Further use of relative terms such as "vertical", "horizontal", "up", "down", and "side-to-side" are used in a relative sense to the normal orientation of the apparatus.

What is claimed is:

1. A resuscitation management system for a manual resuscitator, the system comprising:
a first accelerometer configured to be mounted on a first side of an outer surface of a resuscitation bag of the manual resuscitator, the first accelerometer configured to measure a first acceleration vector for the first side, the first acceleration vector comprising a first acceleration magnitude as a function of time and a first spatial direction of acceleration;

a second accelerometer configured to be mounted on a second side of the outer surface of the resuscitation bag of the manual resuscitator, the second accelerometer configured to measure a second acceleration vector for the second side, the second acceleration vector comprising a second acceleration magnitude as a function of time and a second spatial direction of acceleration, wherein the second side is opposite the first side along a first axis perpendicular to a longitudinal axis of the resuscitation bag; and a processing unit coupled to the first accelerometer and the second accelerometer, the processing unit comprising:

at least one processor; and at least one memory coupled to the at least one processor, the at least one memory storing executable instructions to urge the at least one processor to:

receive the first acceleration vector from the first accelerometer;

receive the second acceleration vector from the second accelerometer;

obtain a resultant acceleration vector by subtracting the second acceleration vector from the first acceleration vector, the resultant acceleration vector comprising an acceleration magnitude as a function of time and a spatial acceleration direction;

calculate a speed of compression/decompression of the resuscitation bag as a function of time for a time interval by integrating the acceleration magnitude as a function of time over the time interval; and calculate an extent of compression/decompression of the resuscitation bag as a function of time for the time interval by integrating the speed of compression/decompression as a function of time over the time interval.

2. The system of claim 1, wherein the at least one memory stores further executable instructions to urge the at least one processor to:

associate each compression/decompression of the resuscitation bag with an adequate ventilation delivered to a patient responsive to the extent of compression/decompression of the resuscitation bag exceeding a predetermined threshold; and calculate a breathing rate delivered to a patient in a time interval by counting adequate ventilations during the time interval.

3. The system of claim 2, wherein the at least one memory further stores executable instructions to urge the at least one processor to calculate an inspiratory to expiratory time (I:E) ratio and breathing pace based at least in part on the calculated speed of compression/decompression of the resuscitation bag as a function of time.

4. The system of claim 2, wherein the at least one memory further stores a calibration correlation between an extent of compression/decompression of the resuscitation bag at a given moment with a volume of breathing gases pushed out of the resuscitation bag at the given moment, the at least one memory further stores executable instructions to urge the at least one processor to calculate a tidal volume for each adequate ventilation delivered to the patient based on the calculated extent of compression/decompression of the resuscitation bag and the stored calibration correlation between the extent of compression/decompression of the resuscitation bag at a given moment with the volume of breathing gases pushed out of the resuscitation bag at the given moment.

5. The system according to claim 4, wherein the at least one memory further stores executable instructions to urge the at least one processor to calculate a minute ventilation by calculating a sum of the calculated tidal volumes for the delivered ventilations in one minute.

6. The system of claim 5, further comprising an input/output (I/O) interface, the processing unit further coupled to the I/O interface, wherein the at least one memory further stores executable instructions to urge the at least one processor to provide information on the I/O interface based at least in part on a plurality of calculated breathing parameters, the plurality of calculated breathing parameters comprising the calculated breathing rate, the calculated I:E ratio, the calculated tidal volume, and the calculated minute ventilation.

7. The system of claim 6, wherein the I/O interface comprises at least one of a visual device, an audio device, a tactile device, and a mechanical device, the information provided by the at least one of the visual device, the audio device, the tactile device, and the mechanical device comprises one or more indications representing the plurality of calculated breathing parameters.

8. The system of claim 7, wherein the I/O interface is configured to produce a plurality of indications, the plurality of indications comprising at least one of a visual indication, an audio indication, a tactile indication, and a mechanical indication.

9. The system of claim 8, wherein the mechanical device comprises:

an attracting element comprising an electromagnet, the attracting element configured to be mounted on the first side of the bag of the manual resuscitator;

an attractable element comprising at least one of a permanent magnet, a ferromagnetic material, and an electromagnet, the attractable element configured to be mounted on the opposite second side of the bag of the manual resuscitator, wherein the at least one memory stores executable instructions to urge the at least one processor to urge the attracting element to attract/repulse the attractable element by applying electrical currents of specific directions and strengths on at least one of the attracting element and the attractable element.

10. The system of claim 9, wherein the at least one memory further storing executable instructions to urge the at least one processor to urge the I/O interface to produce a first indication of the plurality of indications to guide a user to deliver a breathing at a certain instance.

11. The system of claim 9, wherein the at least one memory further stores a plurality of target breathing parameter ranges, the plurality of target breathing parameter ranges comprising a target breathing rate range, a target I:E ratio range, a target tidal volume range, a target minute ventilation range, the at least one memory further storing executable instructions to urge the at least one processor to:

compare a calculated breathing parameter of the plurality of calculated breathing parameters with a corresponding target breathing parameter range of the plurality of target breathing parameter ranges;

urge the I/O interface to produce a first indication of the plurality of indications responsive to the calculated breathing parameter being in the corresponding target breathing parameter range; and urge the I/O interface to produce a second indication of the plurality of indications responsive to the calculated breathing rate being outside the target breathing parameter range.

12. The system of claim 11, wherein the at least one memory stores executable instructions to urge the at least one processor to:
   determine an occurrence of hyperventilation based on the calculated breathing rate, the occurrence of hyperventilation corresponding to the calculated breathing rate being more than the target breathing rate range; and
   urge the mechanical device to lock the bag by urging the attracting element and the attractable element to attract each other responsive to the occurrence of hyperventilation.

13. The system of claim 11, wherein:
   the plurality of target breathing parameter ranges further include subsets of the target breathing parameter ranges, each subset of the subsets of the target breathing parameter ranges associated with at least one of an age group, a medical condition of a patient, and a patient type,
   the I/O interface is further configured to receive data from a user, the data comprising at least one of an age group, a medical condition of a patient, and a patient type,
   the at least one memory further stores executable instructions to urge the at least one processor to:
      select a subset of the subsets of the target breathing parameters based on at least one of the received age group, the received medical condition of a patient, and the received patient type;
      compare each calculated breathing parameter of the plurality of the calculated breathing parameters with a corresponding target breathing parameter range of the selected subset of the subsets of the target breathing parameter ranges;
      urge the I/O interface to produce a first indication of the plurality of indications responsive to each calculated breathing parameter of the plurality of calculated breathing parameters being in a respective target breathing parameter range of the selected subset of the subsets of the target breathing parameter ranges; and
      urge the I/O interface to produce a second indication of the plurality of indications responsive to each calculated breathing parameter of the plurality of the calculated breathing parameters being outside the respective target breathing parameter range of the selected subset of the subsets of the target breathing parameter ranges.

* * * * *